(12) United States Patent
Abry et al.

(10) Patent No.: US 9,486,582 B2
(45) Date of Patent: *Nov. 8, 2016

(54) AUTOMATIC INJECTION DEVICE WITH TEMPORIZING MEANS

(71) Applicant: BECTON DICKINSON FRANCE S.A.S., Le Pont de Claix (FR)

(72) Inventors: Herve Abry, Echirolles (FR); Franck Carrel, Pont de Claix (FR); Guillaume Grunhut, Grenoble (FR); Lionel Maritan, Le Pont de Claix (FR); Frederic Perot, Saint Paul de Varces (FR)

(73) Assignee: Becton Dickinson France S.A.S., Le Pont-de-Claix (FR)

( * ) Notice: Subject to any disclaimer, the term of this patent is extended or adjusted under 35 U.S.C. 154(b) by 621 days.

This patent is subject to a terminal disclaimer.

(21) Appl. No.: 13/864,881

(22) Filed: Apr. 17, 2013

(65) Prior Publication Data

US 2013/0237913 A1    Sep. 12, 2013

Related U.S. Application Data

(63) Continuation of application No. 13/152,336, filed on Jun. 3, 2011, now Pat. No. 8,435,215, which is a continuation of application No. 12/440,145, filed as application No. PCT/IB2007/003451 on Sep. 5, 2007, now Pat. No. 7,976,514.

(30) Foreign Application Priority Data

Sep. 6, 2006   (FR) ...................................... 06 07806

(51) Int. Cl.
A61M 5/20 (2006.01)
A61M 5/00 (2006.01)
(Continued)

(52) U.S. Cl.
CPC ............. *A61M 5/20* (2013.01); *A61M 5/2033* (2013.01); *A61M 5/326* (2013.01); *A61M 5/008* (2013.01);
(Continued)

(58) Field of Classification Search
CPC .............. A61M 2005/206; A61M 2005/2073; A61M 2005/2407; A61M 2005/244; A61M 2005/3109; A61M 2005/3143; A61M 2005/3261; A61M 2205/192; A61M 5/008; A61M 5/20; A61M 5/2033; A61M 5/2053; A61M 5/24
See application file for complete search history.

(56) References Cited

U.S. PATENT DOCUMENTS 4,300,678 A    11/1981   Gyure et al.
5,695,472 A  * 12/1997   Wyrick ......................... 604/136
(Continued)

FOREIGN PATENT DOCUMENTS

EP    1586341 A2    10/2005
EP    1586342 A2    10/2005
(Continued)

*Primary Examiner* — Laura Bouchelle
(74) *Attorney, Agent, or Firm* — The Webb Law Firm

(57) ABSTRACT

The present invention relates to an injection device including a container, intended for receiving a product and provided with an injection needle and a housing receiving the container. The container is movable relative to the housing between an initial position, an insertion position, and a final position. A collapsible chamber is defined within the housing outside of the container. The chamber is collapsible with the container in the insertion position. The chamber is at least partially defined by a proximal wall and a seal element, wherein, with the container in the initial position, the proximal wall is spaced proximally from the seal element, wherein, with the container in the insertion position, the proximal wall is caused to engage the seal element, and, wherein, with the proximal wall engaging the seal element, the container is caused to move from the insertion position to the final position.

9 Claims, 14 Drawing Sheets

Figure 1:
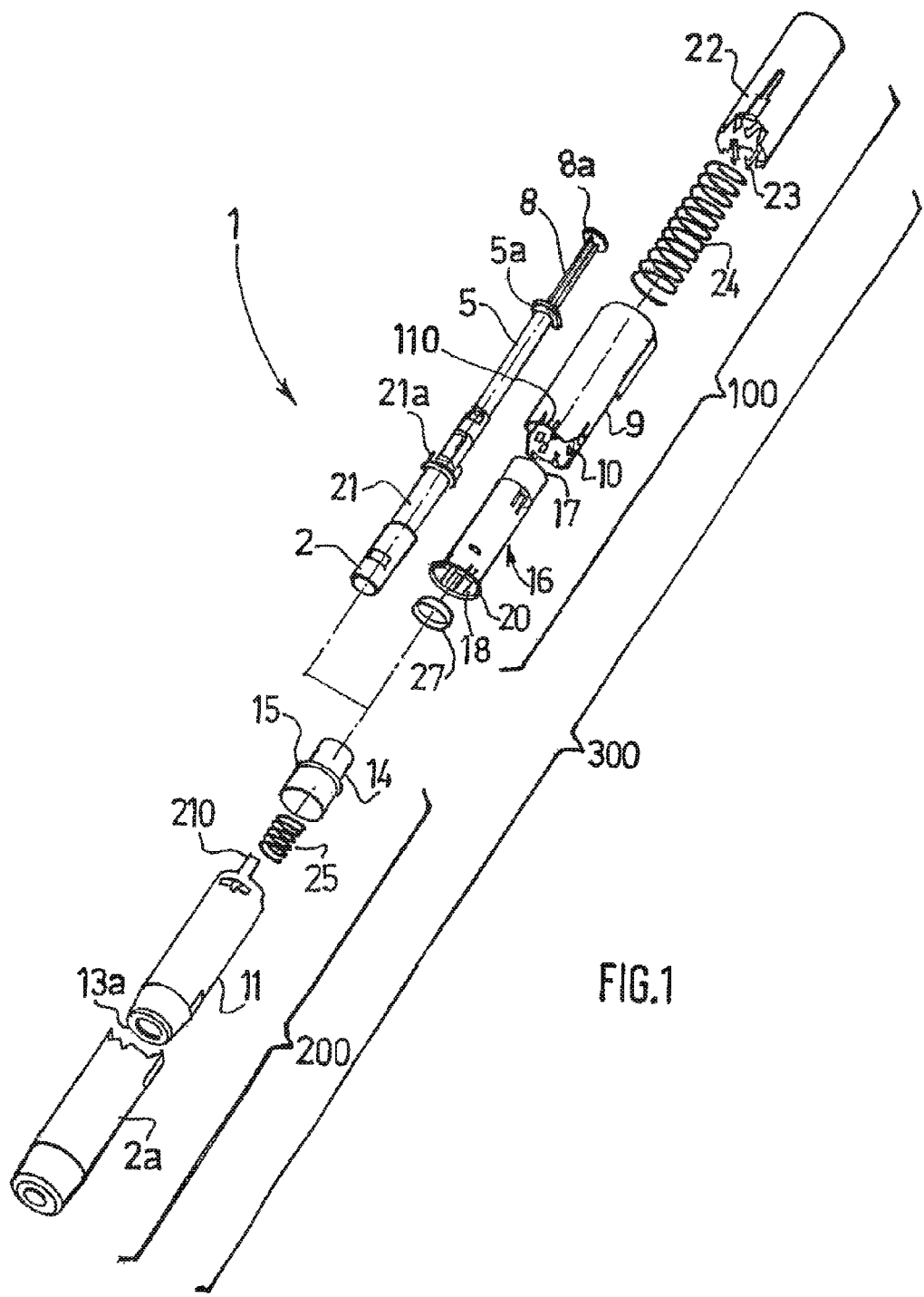

(51) Int. Cl.
  *A61M 5/24* (2006.01)
  *A61M 5/315* (2006.01)
  *A61M 5/32* (2006.01)
  *A61M 5/50* (2006.01)
  *A61M 5/31* (2006.01)

(52) U.S. Cl.
  CPC .............. *A61M 5/2053* (2013.01); *A61M 5/24* (2013.01); *A61M 5/31511* (2013.01); *A61M 5/31525* (2013.01); *A61M 5/31566* (2013.01); *A61M 5/3202* (2013.01); *A61M 5/3204* (2013.01); *A61M 5/5086* (2013.01); *A61M 2005/206* (2013.01); *A61M 2005/2073* (2013.01); *A61M 2005/244* (2013.01); *A61M 2005/2407* (2013.01); *A61M 2005/3109* (2013.01); *A61M 2005/3143* (2013.01); *A61M 2005/3261* (2013.01); *A61M 2205/192* (2013.01)

(56) References Cited

U.S. PATENT DOCUMENTS

| | | | |
|---|---|---|---|
| 6,599,272 B1* | 7/2003 | Hjertman et al. | 604/209 |
| 7,976,514 B2* | 7/2011 | Abry | A61M 5/2033 604/110 |
| 2004/0024367 A1 | 2/2004 | Gilbert | |
| 2005/0165360 A1 | 7/2005 | Stamp | |
| 2009/0088688 A1 | 4/2009 | Donald et al. | |

FOREIGN PATENT DOCUMENTS

| | | |
|---|---|---|
| WO | 9529720 A1 | 11/1995 |
| WO | 0024441 A1 | 5/2000 |
| WO | 03097133 A1 | 11/2003 |
| WO | 2004054645 A1 | 7/2004 |
| WO | 2005115512 A1 | 12/2005 |
| WO | 2005115516 A1 | 12/2005 |
| WO | 2006052737 A1 | 5/2006 |

* cited by examiner

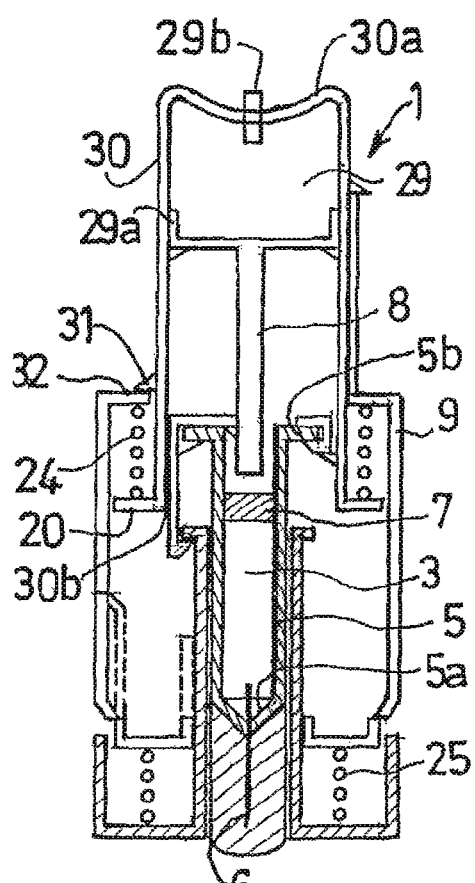
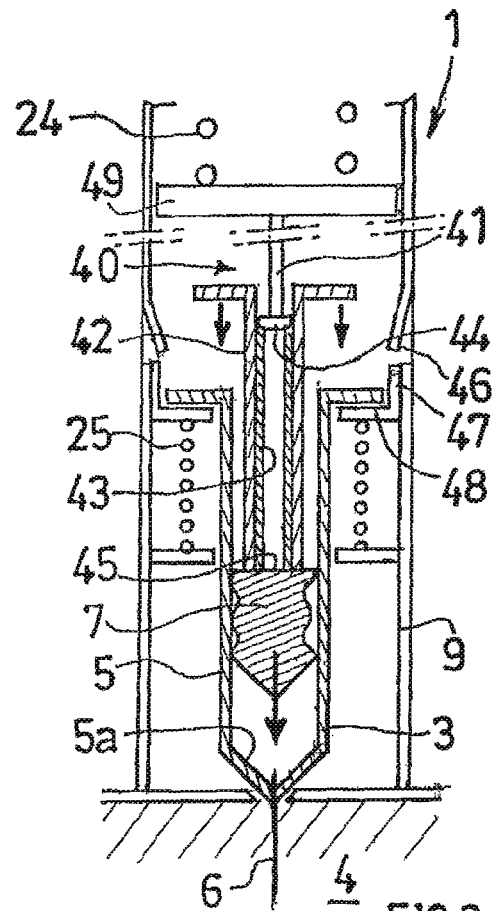
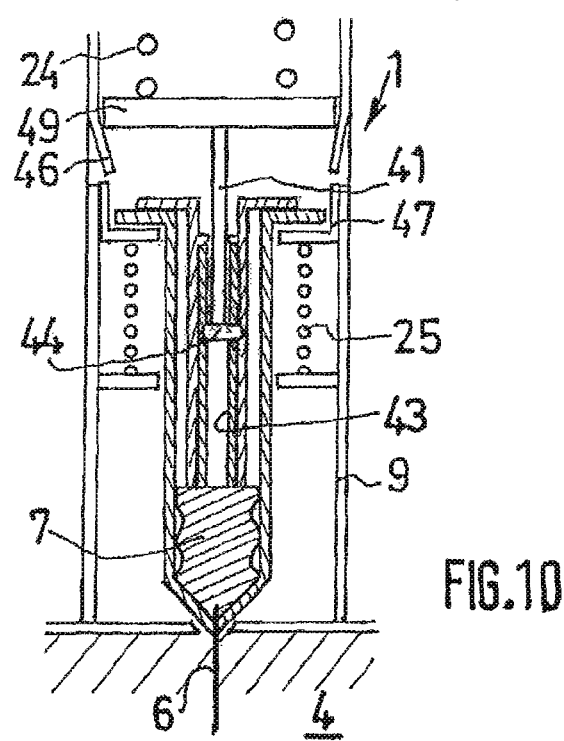

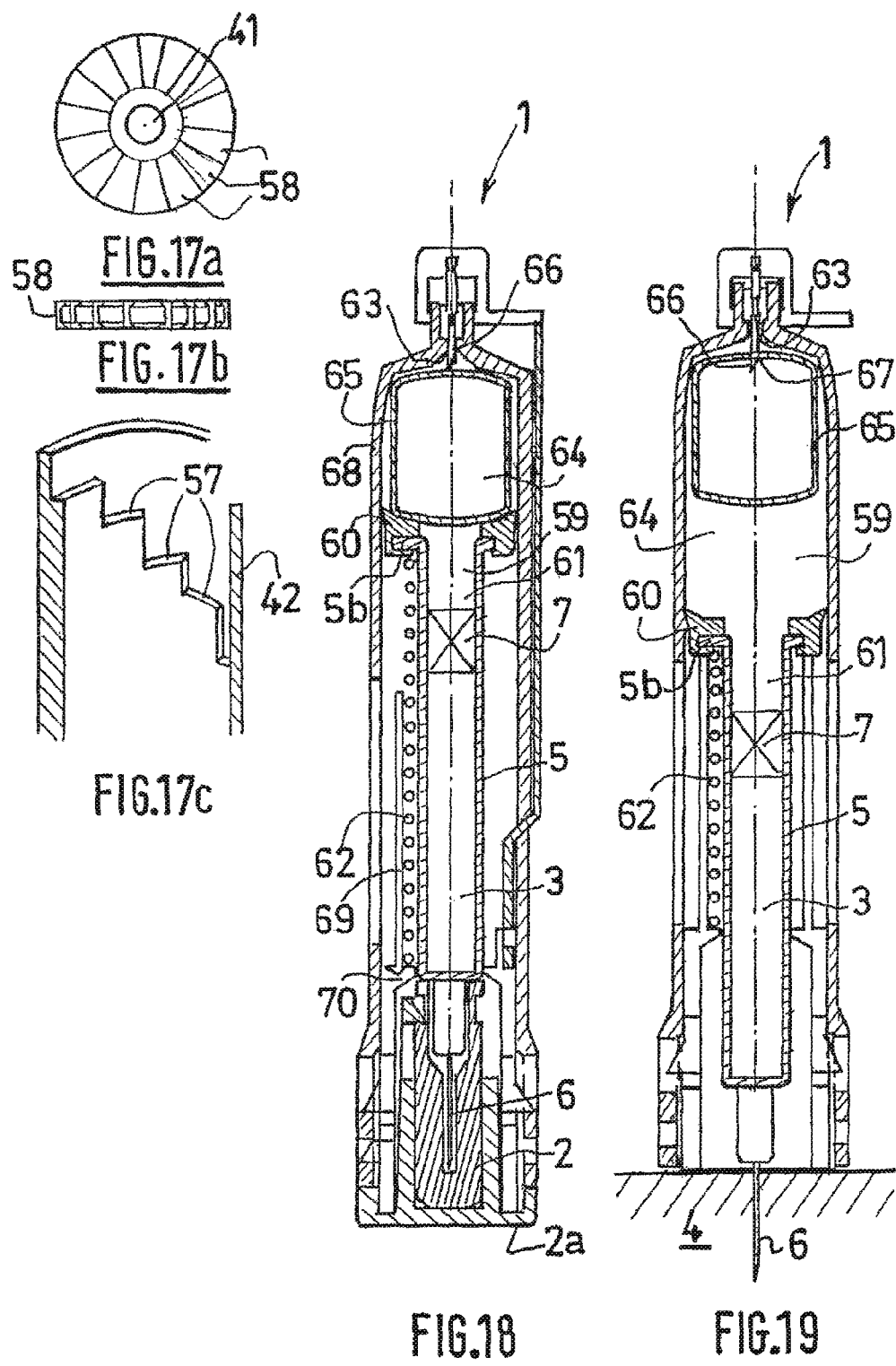

AUTOMATIC INJECTION DEVICE WITH TEMPORIZING MEANS

This application is a continuation of U.S. application Ser. No. 13/152,336, filed Jun. 3, 2011, now allowed, which is a continuation of U.S. application Ser. No. 12/440,145, filed Nov. 23, 2009, now U.S. Pat. No. 7,976,514, which is a National Stage Application under 35 U.S.C. §371 of PCT Application No. PCT/IB2007/003451, filed Sep. 5, 2007, the contents of these applications being incorporated by reference herein.

The present invention relates to a device for automatic injection of a product in a very safe way, especially for self-injection.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

Some illnesses necessitate regular injections of drugs or products, for instance on a daily basis. In order to simplify the treatment, some self-injectors have been provided in order to allow the patient to perform the injection on its own.

Of course, since the patient is usually neither a nurse nor an educated person in medical devices, such self-injectors must prove to be very simple to use and also very safe. In particular, the insertion of the needle must be performed at the right depth, the correct dose of product must be injected, that is to say a complete injection must be performed, and the injector must be deactivated after use before it is disposed of. Preferably, the needle should not be exposed, before and after use, in order to prevent any accidental needlestick injury.

For these reasons, the majority of self-injectors present a high degree of automation. Usually, the user only has to apply the device at the injection site and then to press a button for instance, in order to trigger the insertion of the needle and the automatic injection of the product. In some devices, in particular when the injection is automatic, some damping means are provided in order to control the rate of injection and therefore limit a potential disagreeable feeling for the patient.

EP 1 586 341 and EP 1 586 342 disclose injection devices provided with damping means for controlling the rate of the injection.

As regards the protection of the needle after use, some devices are provided with a sleeve that extends over the needle once the user has removed the device from the injection site. Alternatively, the needle may be automatically retracted within the device at the end of injection with no further action from the user. Therefore, when the user withdraws the device from the injection site, the needle is already retracted within the device and the user does not take the risk to hurt himself.

Nevertheless, one of the problems with self-injectors based on the retraction of the needle is to ensure that the totality of the product has been injected before the needle is retracted. Actually, in most of these devices, because of dimensional tolerances of assembled parts of the device, it is necessary to trigger the retraction of the needle just before the end of complete injection, thereby creating a dead volume at the bottom of the syringe body. The result is that the product dose is not injected completely, which may result in an improper dosage to the patient or user. Documents WO 03/097133 and WO 2005/115512 disclose automatic injection devices comprising means that delay the retraction of the needle at the end of injection and a needle shield.

In consequence, there is a need for self-injection devices that allow the needle to be retracted within the device at the end of an automatically driven injection, with the assurance that the totality of the product has been injected before retraction of the needle.

The present invention meets this need by proposing a device for automatic injection of a product into an injection site, said device allowing both the retraction of the needle at the end of an automatically driven injection and the complete injection of the product.

The present invention relates to a device for automatic injection of a product into an injection site, the injection device comprising:
  a container having an open proximal end and a substantially closed distal end and being intended to receive the product, and provided at its distal end with an injection needle providing an outlet port of said container,
  a housing intended to receive, at least partially, said container, said container being movable relative to said housing between an initial position, in which said needle is contained within said housing, an insertion position, distally spaced relative to said initial position and in which said needle is exposed over a predetermined length, and a final position in which said needle is contained within said housing,
  retaining means, arranged to maintain said container in said insertion position,
  deactivating means, arranged to release automatically said retaining means and cause said container to move to said final position,
  said device being characterized in that it further comprises:
  temporizing means, arranged to control the release of said retaining means by said deactivating means until substantially all of the product contained within said container has been caused to pass through said outlet port and said injection needle before said container moves to said final position, and
  a needle shield coupled with said housing and covering the needle prior to use of said device, removal of said needle shield being with limited or no rotation of said needle shield.

The device of the invention allows that the needle shield be removed before use of the device with limited or no rotation of the needle shield. In consequence, the potential rotation of the tip of the needle within the rubber forming the needle shield is avoided and the core that could result from such a potential rotation is also avoided. The integrity and sterility of the needle are therefore preserved and the administration do the product can be completed safely.

The device of the invention allows the injection of the totality of the product before the needle is retracted. Thanks to the temporizing means of the device of the invention, the retraction of the needle is not triggered when some product is still present at the bottom of the container of the injection device. Some time, for instance between 1 to 10 seconds, is allowed before the retraction of the needle is triggered.

The device of the invention is therefore very safe and very simple of use. The user only needs to apply the device on the injection site and then activate the first deactivating means to start the operation. At the end of the complete injection, and only when all of the product is injected, the needle is retracted within the device and the user can withdraw the device from the injection site without any risk.

In an embodiment of the invention, said housing is coupled to a deshielder comprising a cap to which is fixed said needle shield, said housing comprising grooves for guiding the translation of said cap when said cap is removed together with the removal of said deshielder in view of using said device.

In an embodiment of the invention, said temporizing means comprises a chamber comprising a vent outlet, said chamber being tightly closed by a sealing cover in an initial state, and defining an initial volume of said chamber and in which a determined amount of fluid is contained within said initial volume, said sealing cover being movable within said chamber from said initial state to a final state in which at least part of said fluid has escaped through said vent outlet.

Said vent outlet may be a simple hole, with a small diameter. For instance said diameter may range from 15 micrometer to 25 micrometer. Alternatively, said vent outlet may be an exhaust valve comprising a membrane allowing the passage of the fluid. Said membrane may be made of a material selected from the group comprising polytetrafluoroethylene, polyethylene, paper, tissue, foam, porous plastic, and combinations thereof. The diameter of said membrane may be about 1 mm.

Said fluid may be a gas, like air. Preferably, said fluid is pressurized. Alternatively, said fluid may be a viscous liquid, like oil or grease.

Preferably, said device further comprises elastic return means coupled to said chamber for moving said sealing cover from said initial state to said final state, said deactivating means being coupled to said chamber so that said deactivating means releases said retaining means only when said sealing cover is in said final state.

In an embodiment of the invention, said chamber comprises the proximal part of a sleeve having a closed proximal end and an open distal end, said closed proximal end comprising a vent outlet and said open distal end comprising an outer radial rim, said device further comprising a piston provided in said container and movable with respect to said container, and a plunger rod coupled to said piston so as to cause said piston to move with respect to said container, the movement of said piston causing said product to be expelled from said container through said injection needle,
said sealing cover, in its initial state, closing the inner proximal space of said sleeve thereby defining said chamber, said sealing cover being coupled to said plunger rod,
said outer radial rim being able to cooperate with and release said second retaining means when said sealing cover comes into contact with said closed proximal end of said sleeve.

Advantageously, said device further comprises first elastic return means coupled to said housing for moving said container from said initial position to said insertion position, second elastic return means coupled to said housing for moving said container from said insertion position to said final position, and a ring, said ring being coupled to said container at least from said insertion position to said final position of said container,
said retaining means comprises a flexible tongue provided on said housing and engaged on an abutment surface situated on said ring, when said container is in said insertion position,
said outer radial rim deflecting said flexible tongue and thereby disengaging said tongue from said ring, when said sealing cover comes into contact with said closed proximal end of said sleeve, thereby freeing said second elastic return means and causing said container to move to said final position.

Preferably, the device of the invention further comprises first retaining means, arranged to maintain said container in said initial position, and first deactivating means, arranged to release said first retaining means and cause the insertion of said needle at the injection site, wherein said first retaining means comprises a flexible tooth provided on said housing, said flexible tooth being engaged with said outer radial rim of said sleeve when said container is in said initial position,
said first deactivating means comprises a push button comprising at least one distal leg,
said distal leg cooperating with at least said flexible tooth so as to deflect and disengage said flexible tooth from said outer radial rim, under the effect of a manual pressure exerted on said push button, thereby freeing said first elastic return means and causing said container to move from said initial position to said insertion position.

In another embodiment of the invention, said sleeve forms said first deactivating means, said first retaining means comprising an outer projection provided on said sleeve, said outer projection being in abutment against a stop provided on said housing and preventing the distal translation of said sleeve when said container is in said initial position, said stop being able to be overcome by said outer projection under manual pressure exerted on said sleeve, thereby freeing said first elastic return means and causing said container to move from said initial position to said insertion position.

In a further embodiment of the invention, said device further comprises a piston provided in said container and movable with respect to said container, a plunger rod coupled to said piston so as to cause said piston to move with respect to said container, the movement of said piston causing said product to be expelled from said container through said injection needle, second elastic return means coupled to said housing for moving said container from said insertion position to said final position, and automatic injection means, arranged to automatically cause said plunger rod to push distally said piston,
said deactivating means being formed on the proximal part of said plunger rod and said retaining means being partly formed on said housing,
said plunger rod being provided in two parts, a proximal part and a distal part, when said piston comes into contact with the distal end of said container, under the force exerted by said automatic injection means on the proximal part of said plunger rod, wherein said distal part of said plunger rod is thereby stopped and said proximal part of said plunger is allowed to continue its distal movement under the force exerted by said automatic injection means for a certain time until said deactivating means cooperate with said retaining means to cause said container to move from said insertion position to said final position, said proximal part of said plunger rod forming part of said temporizing means.

Advantageously, said device further comprises a ring, said ring being coupled to said container when said container moves from said insertion position to said final position,
said retaining means comprises a radially flexible leg situated on the inner wall of said housing, engaged on an abutment surface of said ring, when said container is in said insertion position, said deactivating means comprises a head of said proximal part of said plunger rod, said plunger rod head deflecting said radially flexible leg under the force exerted by said automatic injection means, thereby disengaging said radially flexible leg from said abutment surface, freeing said second elastic return means and causing said container to move from said insertion position to said final position.

Preferably, said distal part of said plunger rod comprises a cylinder capable of receiving a portion of said proximal part of said plunger rod, and said distal part of said plunger rod comprises softening means designed for reducing the speed of the distal movement of said proximal part of said plunger rod within said distal part of said plunger rod.

In an embodiment of the invention, said softening means comprise a rubbery material coated on the inner wall of said cylinder, said proximal part of said plunger rod being provided at its distal end with at least one radial projection that contacts said rubbery material as said proximal part of said plunger rod moves distally. By contacting said rubbery material, the proximal part of the plunger rod is slowed down and some time is therefore provided for the rest of the product to be completely expelled through the needle before the second deactivating means release the second retaining means and cause the container to move to its final position.

In another embodiment of the invention, said softening means comprise a compressible material provided at the bottom of said cylinder, the speed of said proximal part of said plunger rod being reduced when the distal end of said proximal part of said plunger rod comes in contact with said compressible material. Said compressible material may be a spring. By reducing the speed of the proximal part of the plunger rod, some time is allowed for the totality of the product to be expelled before the container is caused to move to its final position.

In a further embodiment of the invention, the inner diameter of said cylinder decreases towards the bottom of said cylinder and the distal end of said proximal part of said plunger rod is provided with flexible tongues that rub against the inner walls of said cylinder as said proximal part of said plunger rod moves distally.

In another embodiment of the invention, the inner walls of said cylinder are provided with longitudinal flexible legs that come in contact with a radial projection provided at the distal end of said proximal part of said plunger rod, thereby reducing the speed of said proximal part of said plunger rod, as said proximal part of said plunger rod moves distally.

In a further embodiment of the invention, said inner walls of said cylinder are provided with a thread which cooperates with a screw provided at the distal end of said proximal part of said plunger rod, thereby reducing the speed of said proximal part of said plunger rod, as said proximal part of said plunger rod moves distally.

In another embodiment of the invention, said cylinder walls are provided with a number of steps and the distal end of said proximal part of said plunger rod is provided with a number of radial flaps, the number of radial flaps that interact with said steps increasing as said proximal part of said plunger rod moves distally. In consequence, the more the proximal part of said plunger rod moves distally, the greater is the resistance force resulting from the interaction of the flaps with the steps. The proximal part of the plunger rod is therefore slowed down and some time is therefore allowed for the totality of the product to be expelled before the container is caused to move to its final position.

In an embodiment of the invention, the device further comprises first retaining means arranged to maintain said container in said initial position, and first deactivating means arranged to release said first retaining means and cause the insertion of said needle at the injection site, wherein said first deactivating means are manually actuated.

In a further embodiment of the invention, the device further comprises means for indicating to a user that substantially all of the product contained within said container has been caused to pass through said outlet port and said injection needle.

In another embodiment of the invention, the device further comprises tamper-evidence means removably coupled with said housing to shield said needle prior to use of said device, said tamper-evidence means being in one of a pre-use condition and a post-use condition, said post-use condition preventing re-use of said tamper evidence means with said device.

Preferably, said post-use condition provides a visual indication that said tamper evidence means has been removed from said device.

In an embodiment of the invention, said tamper-evidence means comprises a deshielder and a needle shield, said post-use condition proving an indication that said temper-evidence means has been removed from said device.

In an embodiment of the invention, the device further comprises a needle shield coupled with said housing and covering the needle prior to use of said device, removal of said needle shield being with limited or no rotation of said needle shield.

In another embodiment of the invention:
said device further comprising a piston provided in said container and movable within said container, the distal movement of said piston causing said product to be expelled from said container through said injection needle,
said chamber being partly defined by the inner part of the container situated proximally to said piston and partly defined by the proximal part of said housing, said sealing cover joining the proximal end of said inner part to said housing through a friction force of absolute value F,
said chamber being filled in said initial state of said sealing cover with a pressurized fluid exerting a pressure of absolute value Pc on said container in the distal direction, with the intermediary of the piston,
said device further comprising elastic return means for moving said container from the insertion position to the final position, said elastic return means being coupled to said container so as to exert on said container a return force of absolute value Pe when said elastic return means is at least in a partly compressed state,
wherein Pc is strictly greater than (Pe+F) in the initial state of the sealing cover,
wherein Pc decreases as part of the pressurized fluid is escaping the chamber via the vent outlet,
said retaining means are formed by Pc being greater than (Pe+F), said retaining means being released when Pe becomes equal or greater than (Pc+F).

Preferably, said pressurized fluid is provided to said chamber from a recipient present within said chamber, said recipient being sealingly closed when said container is in its initial position, said device being provided with a puncturing button capable of creating an opening in said recipient when a manual force is exerted on said puncturing button, said pressurized fluid being then allowed to escape from said recipient and to fill said chamber.

In another embodiment of the invention, said sealing cover is porous and forms said vent outlet. Preferably said device further comprises:
- a piston provided in said container and movable within said container, the distal movement of said piston causing said product to be expelled from said container through said injection needle,
- a piston rod provided with a head and a distal end, said piston rod being independent from said piston, said chamber is defined by the volume delimited by the inner part of the container situated proximally to said piston, the wall of the housing and the head of the piston rod, the proximal end of said container joining the wall of the housing via a first porous sealing cover and the head of the piston rod joining the wall of the housing via a second porous sealing cover.

In an embodiment of the invention, the two sealing covers present a friction force against the wall of said housing of absolute value F,
- said chamber is filled in the initial state of said second sealing cover with a pressurized fluid exerting a pressure of absolute value Pc on said container in the distal direction, with the intermediary of the piston,
- said device further comprising first elastic return means for moving said container from the initial position to the insertion position, said first elastic return means being coupled to said piston rod so as to exert on said piston rod a return force of absolute value Pi when said first elastic return means is at least in a partly compressed state,
- said device further comprising second elastic return means for moving said container from the insertion position to the final position, said second elastic return means being coupled to said container so as to exert on said container a return force of absolute value Pe when said second elastic return means is at least in a partly compressed state,
- wherein (Pc+Pi) is greater than (Pe+F) in the initial state of said second sealing cover,
- wherein Pc decreases as part of the pressurized fluid is escaping the chamber via the vent outlet,
- said retaining means are formed by (Pc+Pi) being greater than (Pe+F), said retaining means being released when Pe becomes equal or greater than (Pc+F+Pi).

In another embodiment of the invention, the deactivating means comprise a valve situated on said first porous sealing cover, said valve being closed when said second porous sealing cover is in its initial state and opened when said second porous sealing cover is in its final state, the opening of said valve releasing part of said retaining means.

Another aspect of the invention is a kit for a device for automatic injection of a product into an injection site, the product being carried by a container having an open proximal end and a substantially closed distal end and having a reservoir defined therebetween, and a needle provided at the distal end and in fluid communication with the reservoir to provide an outlet port for the product from the container, and a piston provided in the container and movable with respect with the container, the movement of the piston causing the product to be expelled from the container through the needle, characterized in that said kit comprises:
- a housing assembly comprising:
    - an upper housing assembly,
    - a lower housing assembly, at least one of said upper and said lower housing assembly being adapted to receive part of the container, the container being movable, when received within said at least one of said upper and said lower housing assembly, between an initial position, in which a tip of said needle does not extend beyond a distal end of said lower housing assembly, an insertion position, distally spaced relative to said initial position and in which the tip of the needle extends beyond said distal end of said lower housing assembly, and a final position in which said needle is contained within one of said upper and said lower housing assembly, and
- means for connecting said upper housing and said lower housing together.

Preferably, said kit further comprises means for carrying at least one of said upper housing assembly and said lower housing assembly, said carrying means carrying said one of said upper housing assembly and said lower housing assembly in a predetermined orientation.

Figure 2:
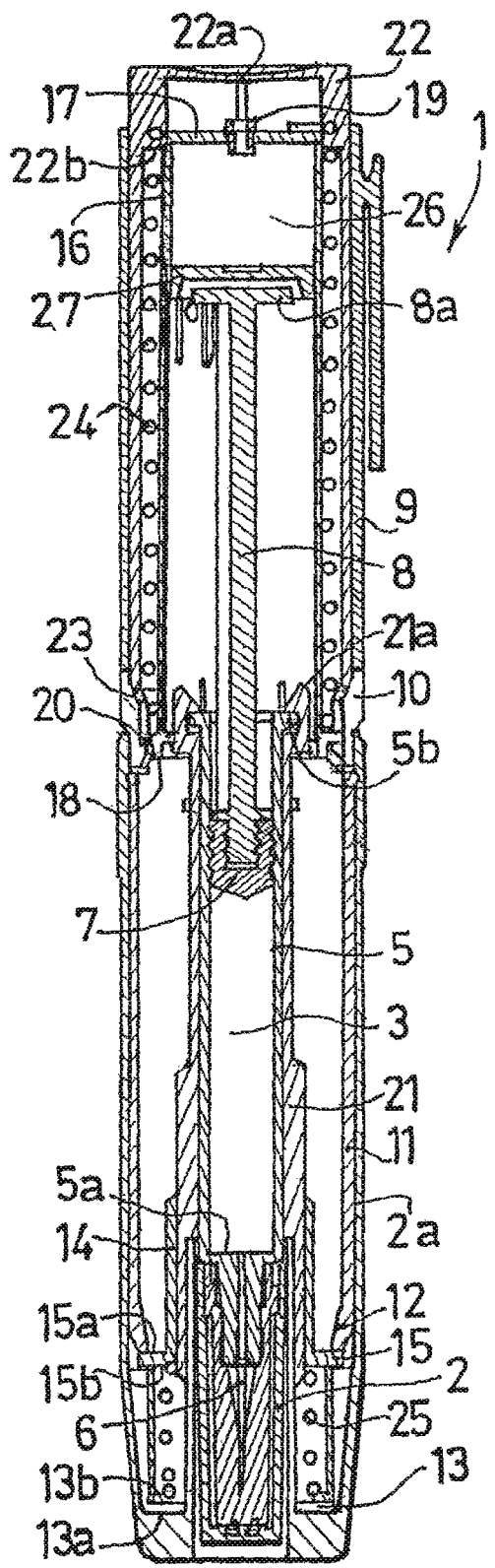
Figure 3:
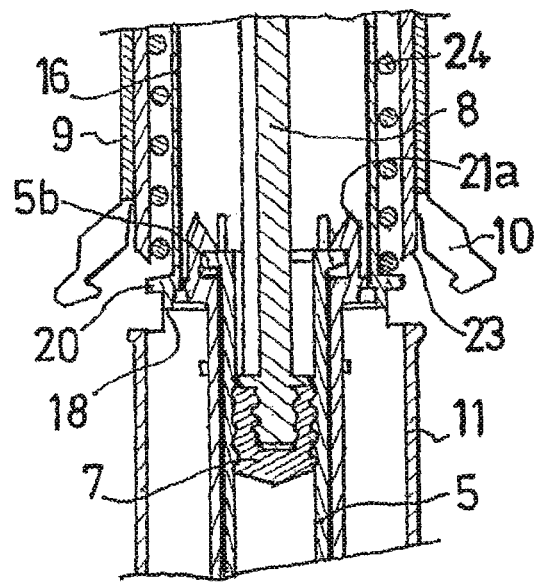
Figure 4:
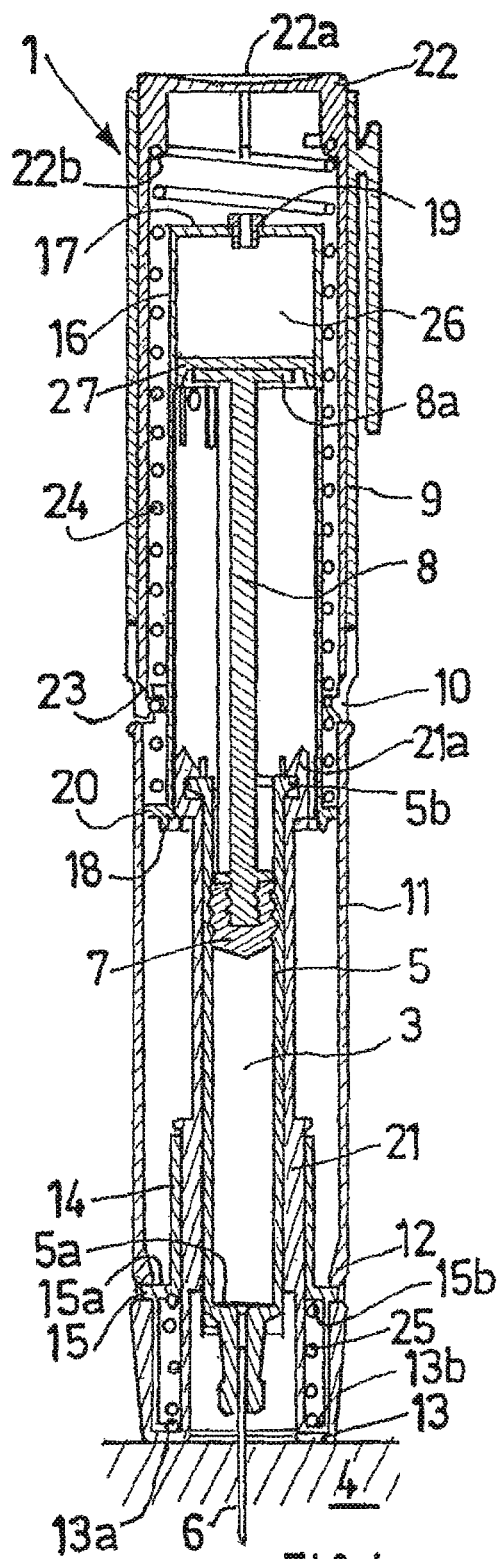
Figure 5:
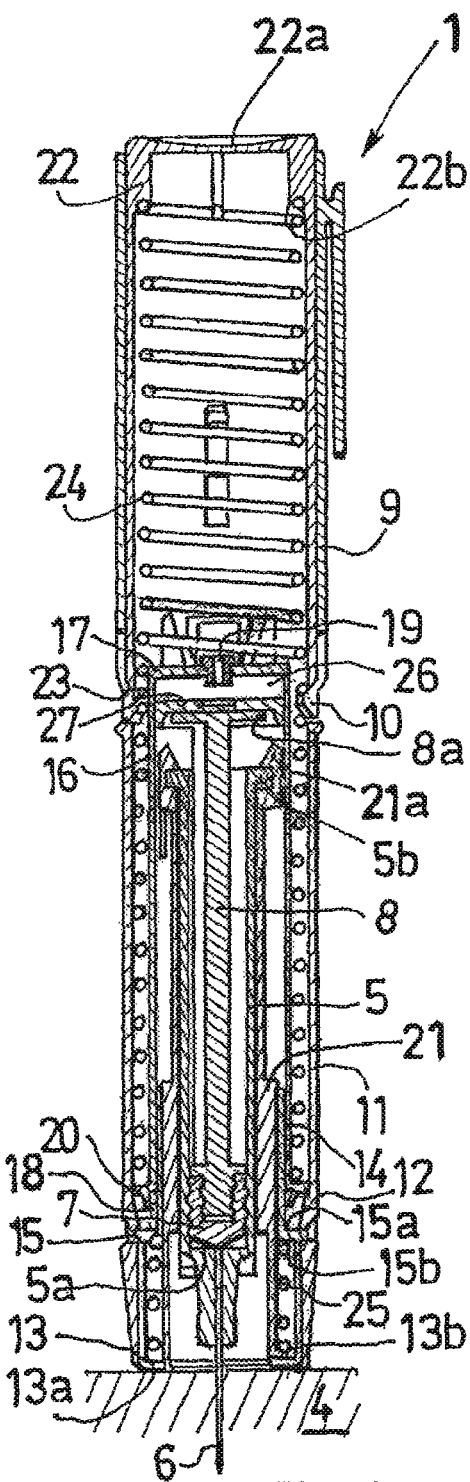
Figure 6:
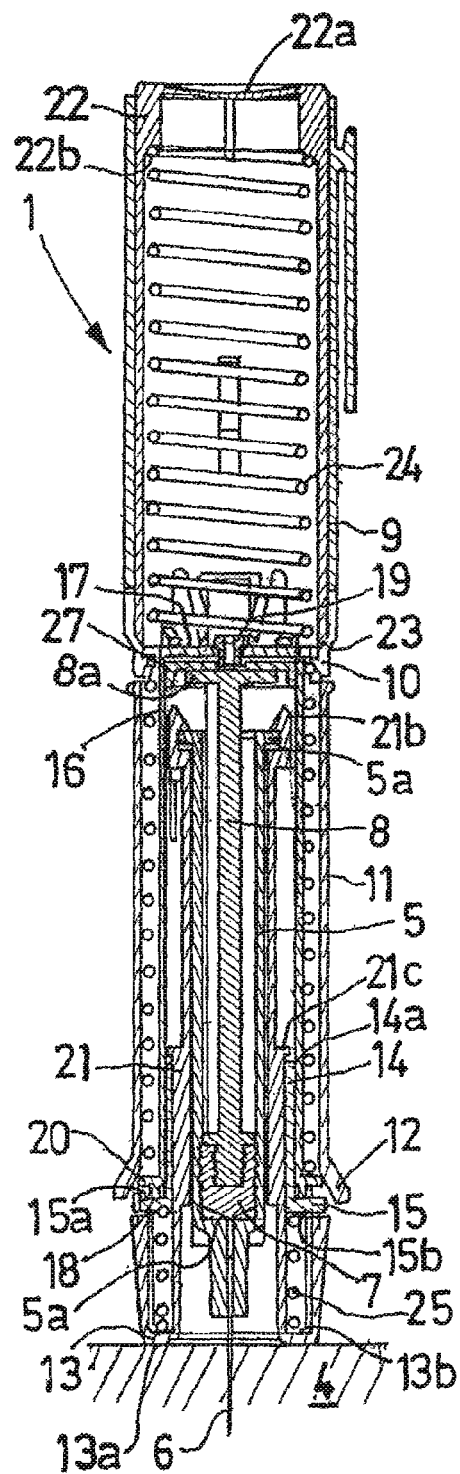
Figure 7:
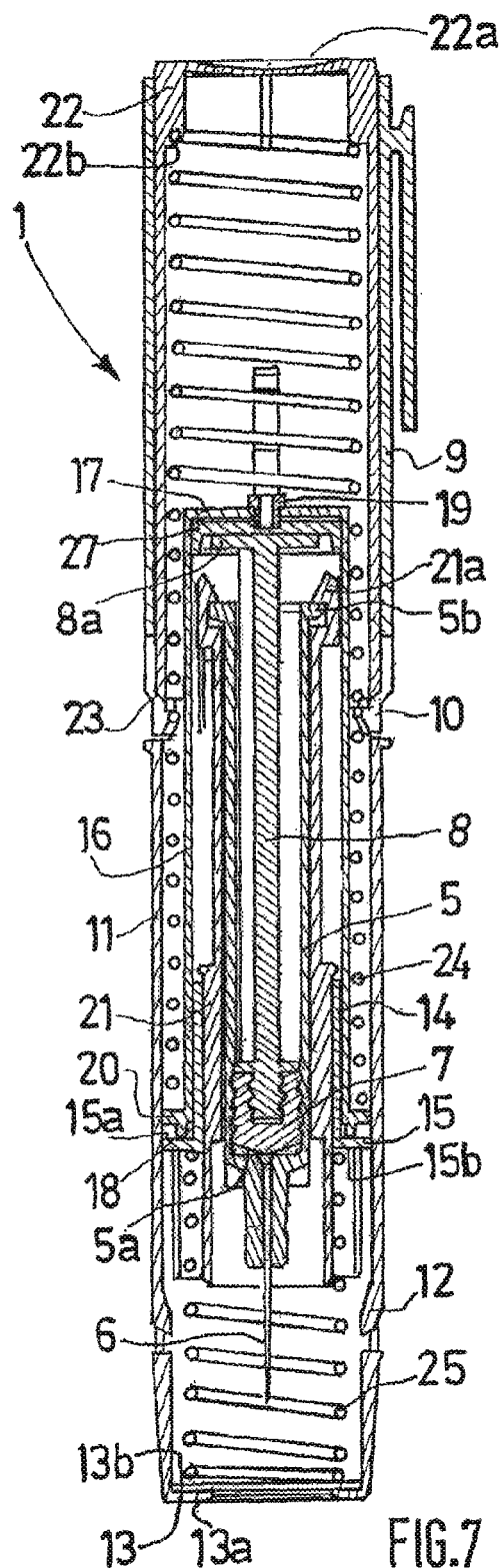
Figure 11:
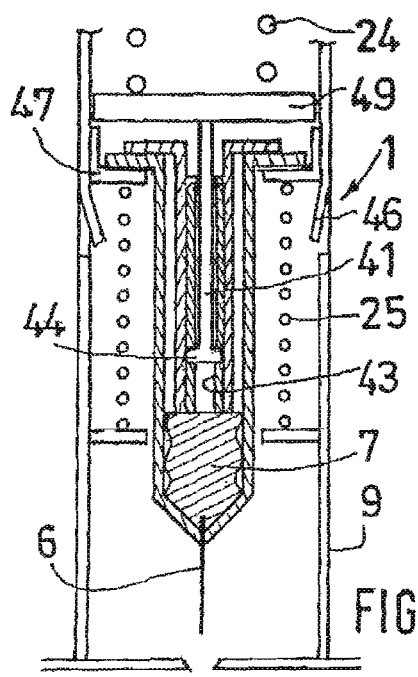
Figure 26:
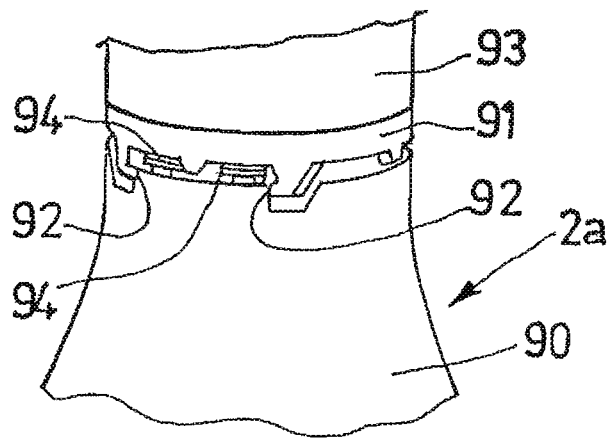
Figure 27:
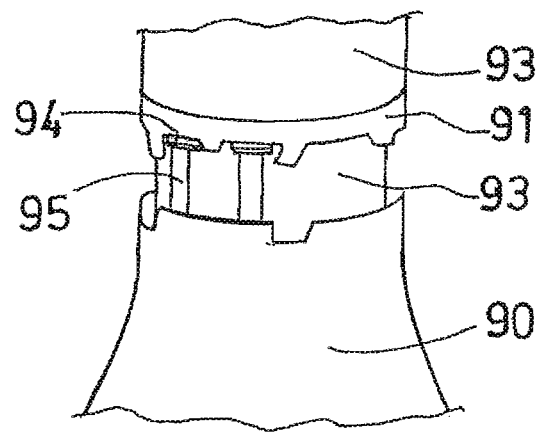
Figure 28:
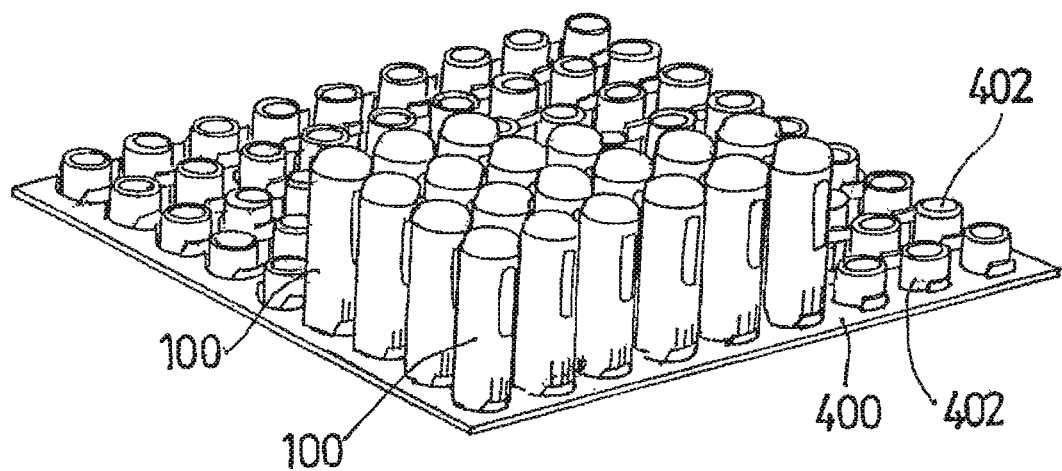
Figure 29:
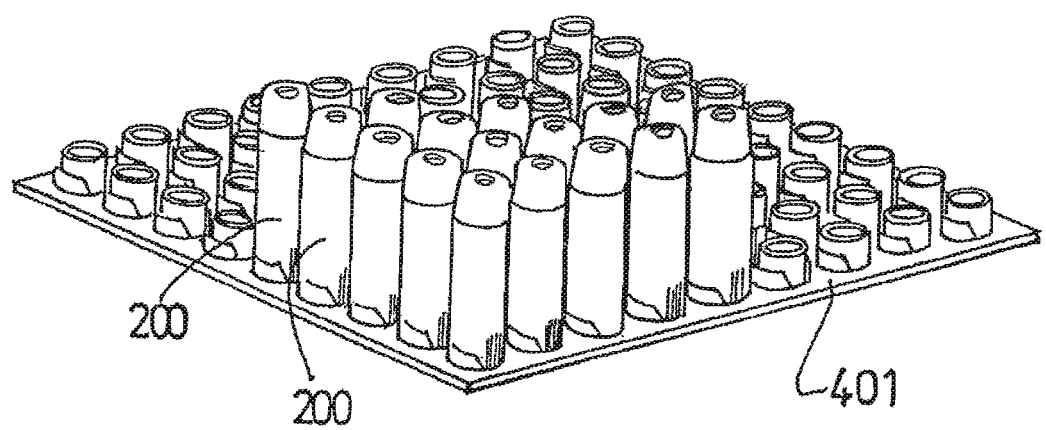

The device of the invention will now be further described in reference to the following description and attached drawings in which:

FIG. 1 is an exploded perspective view of an embodiment of the device of the invention, FIG. 2 is a cross section view of the device of FIG. 1 before use, FIG. 3 is a partial cross section view of the device of FIG. 1 showing the deactivation of the first retaining means, FIG. 4 is a cross section view of the device of FIG. 1 with the container in the insertion position, FIG. 5 is a cross section view of the device of FIG. 1 in the injection step, before temporization, FIG. 6 is a cross section view of the device of FIG. 1 at the end of temporization, FIG. 7 is a cross section view of the device of FIG. 1 with the container in the final position, FIG. 8 is a cross section view of a variant of the device of the invention, FIGS. 9 to 11 are cross section views of a further variant of the device of the invention, respectively during the injection step, during the temporization step, and in the final position, FIGS. 12 to 16 are partial cross section views of various mechanical temporizing means, FIG. 17a is a front view of the distal end of the proximal part of a plunger rod suitable for forming part of the temporizing means of the device of the invention, FIG. 17b is a side view of the distal end of the proximal part of the plunger rod of FIG. 17a, FIG. 17c is a cross section view in perspective of the distal part of the plunger rod of FIG. 17a, FIGS. 18 to 21 are cross section views of an alternative of the device of the invention, respectively in the initial position, in the insertion position, in the end-of-injection position, and in the final position, FIGS. 22 to 25 are cross section views of another variant of the device of the invention, respectively in the initial position, in the insertion position, in the end-of-injection position, and in the final position, FIGS. 26 and 27 are partial side views of a tamper-evidence means suitable for the device of the invention, respectively in the pre-use condition and in the post-use condition, FIGS. 28 and 29 are perspective views of means for carrying at least one of the upper housing and the lower housing of a device of the invention, FIGS. 30 to 33 are cross section views of another variant of the device of the invention, respectively in the initial position, in the insertion position, in the end-of-injection position, and in the final position.

FIG. 1 shows an exploded perspective view of a device for automatic injection according to an embodiment of the present invention and generally designated by reference number 1. The inventive device 1 comprises a housing 300 comprised of an upper housing assembly 100 and a lower housing assembly 200 that may be connected to each other by means of a snap-fit connection (110, 210) like screw-type connection, bayonet connection, or other means of connecting two parts together, in an unreleasable way or not. When the device of the injection is of a single use type, the means for connecting the upper housing assembly 100 to the lower housing assembly 200 are made unreachable to the user. A container 5 such as, for example, a syringe, is received in at least one of the upper and lower housing assemblies (100, 200). Preferably, the container 5 is partially received in each of the upper and lower housing assemblies (100, 200), as discussed in more detail herein.

In reference to FIGS. 1 and 2, the injection device comprises a container 5 which is intended to receive a product 3 that is to be injected. The container 5 has a distal end 5a and an open proximal end, which is provided, on the example shown, with a flange 5b. Said flange 5b may be useful for grasping said container 5. The distal end 5a of the container 5 is substantially closed and is provided with an injection needle 6. This injection needle 6 provides an outlet port of said container 5 for the product 3. On FIGS. 1 and 2, the distal end of said container 5 is also provided with a needle shield 2 that covers and protects the needle 6 before use of the device 1. The needle shield 2 also provides for a sealing means of the distal end of the container 5 before use.

The device 1 of FIGS. 1 and 2 also comprises a piston 7 which is provided in the container 5 and which is movable with respect with said container 5. A plunger rod 8 is coupled to, said piston 7 so as to cause said piston to move with respect to said container 5, the movement of said piston 7 being intended to cause said product 3 to be expelled from said container 5 through the injection needle 6 during the injection step and thus realize injection, as will be seen on FIGS. 4 to 6. As used herein, the term "coupled" refers to any permanent or temporary connection between two parts. For example, by way of illustration and not limitation, two parts may be coupled together using a screw-type connection, by mere contact with each other, or with adhesive. Other types and ways of connecting two parts will be obvious to a person skilled in the art and from the disclosure provided herein.

The container 5 is received within a support 21 having a global tubular shape: said support 21 is open at both ends. Said support 21 is provided at its proximal end with at least two claws 21a in which the flange 5b of the container 5 is fixed.

The device 1 of FIGS. 1 and 2 further comprises a housing (9, 11) intended to receive the container 5. In the example shown, said housing has a global tubular shape and is made of two cylinders, a proximal cylinder 9 and a distal cylinder 11 which, as shown on FIG. 2, are snapped to each other when the device is in use. In an embodiment of the invention not shown, the housing (9, 11) could be made of a single piece. The needle shield 2 is coupled to the housing (9, 11) and covers the needle 6 prior to use of the device 1. In particular, as appears clearly from FIG. 2, the device 1 is provided with a deshielder 2a to which is fixed the needle shield 2. Such a deshielder 2a is shown in greater details on FIGS. 26 and 27. The housing (9, 11) of the device 1 is coupled to the deshielder 2a which comprises a cap 90 to which is fixed the needle shield 2. As shown on FIG. 27, the housing comprises grooves 95 for guiding the translation of said cap 90 when the cap 90 is removed together with the removal of said deshielder 2a in view of using said device 1. In consequence, when the user removes the deshielder 2a in order to use the device 1, the cap 90 follows the grooves 95 and it does not rotate. The needle shield 2, which is fixed to the cap 90, neither rotates. The rotation of the tip of the needle 6 within the rubber forming the needle shield is therefore avoided and the core that could result from such a potential rotation is also avoided. The integrity and sterility of the needle 6 are therefore preserved and the administration do the product can be completed safely.

As will appear later, the container 5 is movable relative to said housing (9, 11) between an initial position, in which said needle 6 is contained within said housing (9, 11), an insertion position, distally spaced relative to said initial position and in which said needle 6 is exposed over a predetermined length, and a final position in which said needle 6 is contained within said housing (9, 11).

The proximal cylinder 9 of the housing is provided at its distal end with at least two flexible teeth 10 which are capable of being deflected radially and outwardly.

As shown on FIG. 2, the distal cylinder 11 of the housing is provided in its distal part with at least two flexible tongues 12 which are capable of being deflected radially and outwardly. The distal end of said distal cylinder 11 is provided with an inner ridge 13: the distal face 13a of said inner ridge forms a bearing surface for the device 1 on the injection site 4 (see FIG. 4).

The device 1 of FIGS. 1 and 2 further comprises a sleeve 16 having a closed proximal end 17 and an open distal end 18. Said sleeve 16 is intended to receive at least partially said support 21. The proximal end 17 of the sleeve 16 comprises a vent outlet 19. The vent outlet 19 may be a little hole. For instance, the diameter of said hole may range from 15 micrometer to 25 micrometer. Alternatively, the hole is replaced by a membrane vent. In such a case, the diameter of said membrane may be about 1 mm. The distal end 18 of said sleeve 16 is provided with an outer radial rim 20.

The device 1 of FIGS. 1 and 2 further comprises a sealing cover 27 which is intended to be coupled to the head 8a of the plunger rod 8.

The device 1 of FIGS. 1 and 2 also comprises a ring 14 which is intended to receive the distal part of said support 21 and to be coupled to said container 5 at least from the insertion position to the final position of said container 5. The ring 14 has a proximal part and a distal part, the diameter of said proximal part being less than the diameter of said distal part, said proximal and distal parts being joined by a radial wall 15. The radial wall 15 has a proximal face 15a and a distal face 15b.

The device 1 of FIGS. 1 and 2 further comprises a push button 22 intended to be lodged between the proximal cylinder 9 of said housing and said sleeve 16. The push button 22 has the global shape of a cylinder closed at its proximal end: the proximal end of the push button 22 forms a pushing surface 22a for the user to exert a manual pressure in view of triggering of the device 1. The inner wall of the proximal part of the push button 22 is provided with an inner rim 22b. The push button 22 is further provided at its distal end with at least two distal legs 23.

In the device 1 according to FIGS. 1 and 2, a first helicoidal spring 24 is provided between the push button 22 and the sleeve 16. As appears from FIG. 2, the distal end of the first helicoidal spring bears on the proximal face of said outer radial rim 20 of said sleeve 16, and the proximal end of the first helicoidal spring bears on the distal face of the inner rim 22b of the push button 22. A second helicoidal spring 25 is provided between said support 21 and said ring 14: as shown on FIG. 2, the distal end of the second helicoidal spring 25 bears on the proximal face 13b of the inner ridge 13 of the distal cylinder 11 and the proximal end of said second helicoidal spring 25 bears on the distal face 15b of said radial wall 15 of said ring 14.

The device 1 of FIGS. 1 and 2 is finally provided with a deshielder 2a for removing the needle shield 2 when the user decides to realize the injection. As will be seen later, the deshielder 2a and the needle shield 2 are removably coupled with the housing (9, 11) and they act as tamper-evidence means to shield the needle 6 prior to use of the device 1, said tamper-evidence means being able to adopt a pre-use condition and a post-use condition, said post-use condition preventing re-use of the tamper-evidence means with the device 1.

The functioning of the device 1 will now be explained in reference to FIGS. 2 to 7.

On FIG. 2 is shown the device 1 before use, as provided to the user. In this position, the sealing cover 27 is in an initial state wherein it tightly and sealingly closes the proximal part of said sleeve 16, thereby defining a chamber 26 having an initial volume. In the position of FIG. 2, said initial volume of said chamber 26 contains a determined amount of pressurized fluid, for example of pressurized air. Alternatively, the fluid could be another gas or a viscous liquid, such as oil or grease. As will be seen later, the sealing cover 27 is movable between said initial state and a final state in which at least part of said pressurized fluid has escaped through the vent outlet 19.

In the position before use as shown on FIG. 2, the container is in its initial position. It is retained in said initial position by the engagement of said flexible teeth 10 of said proximal cylinder 9 in said outer radial rim 20 of said sleeve 16, said flexible teeth 10 and said outer radial rim 20 acting as first retaining means, under the pressure of said first helicoidal spring 24, which is in a pressurized state.

In this position, the needle 6 is protected by the needle shield 2 which is coupled the deshielder 2a. Accordingly, the deshielder 2a and the needle shield 2 form the tamper-evidence means which is in its pre-use condition.

When the user decides to realize the injection, he first removes the deshielder 2a: by this operation, he also removes the needle shield 2. The tamper-evidence means, formed by the deshielder 2a and the needle shield 2 is therefore in its post-use condition. The removal of the needle shield 2 is completed with limited or no rotation of the needle shield 2. Potential coring caused by the tip of the needle 6 rotating in the rubber forming the needle shield 2 is therefore prevented.

After deshielding, the container 5 is still retained in its initial position by the first retaining means which are in the same position as described in FIG. 2.

In a step not shown, the user then applies the device 1 on the injection site 4 by means of the bearing surface 13a of said distal cylinder 11. He then manually actuates the push button 22 by exerting on the pushing surface 22a a distal force so as to cause said push button 22 to move distally.

As shown on FIG. 3, during this movement, the distal legs 23 come in contact with said flexible teeth 10, causing said flexible teeth 10 to deflect radially and outwardly. By way of consequence, said flexible teeth 10 are disengaged from said outer radial rim 20 in which they were previously engaged. The first helicoidal spring 24 is therefore free to return to a normal state and it extends distally, drawing with him the sleeve 16. The sleeve 16 being coupled to said plunger rod 8 by means of the sealing cover 27 which is fixed onto the head 8a of the plunger rod 8, the plunger rod 8 is drawn distally by the sleeve 16. Moreover, the distal end of the plunger rod 8 being threaded within the piston 7, the plunger rod 8 is coupled to said container 5, at least from the initial position to the insertion position of the container, by means of the friction force exerted by the outer walls of said piston 7 onto the inner walls of said container 5. In consequence, the container 5 is also drawn distally causing the needle 6 to penetrate the injection site 4 until the distal end of said support 21 abuts on the proximal face 13b of the inner ridge 13 of said distal cylinder 11, as shown on FIG. 4.

As shown on FIG. 4, the container 5 is therefore in the insertion position and the injection of the product 3 can start. The injection is automatically driven by means of the first helicoidal spring 24 which continues to extend distally towards its normal state. Once the container 5 is prevented from moving distally by means of said support 21 being stopped against the inner ridge 13, the force of the first helicoidal spring 24 overcomes the stiction force and the piston 7 is caused to move distally within said container 5, thereby expelling said product 3 through said injection needle 6.

Once the piston 7 is proximate to said distal end 5a of the container 5 and abuts more or less on said distal end 5a, the force of said first helicoidal spring 24 overcomes the friction force of the sealing cover 27 against the inner walls of said sleeve 16 and said sleeve continues to move distally, causing part of the pressurized fluid present in said chamber 26 to escape via the vent outlet 19, as shown on FIG. 5.

As shown on FIG. 5, in the device 1 of the invention, although the piston 7 has reached the distal end of the container 5, said container 5 is prevented from moving from its insertion position to its final position, as long as substantially all the product has not been expelled, and especially as long as said sealing cover 27 has not reached its final state (see FIG. 6): indeed, as clearly appears from FIG. 5, the second helicoidal spring 25, which is intended to move said container from its insertion position to its final position, is still prevented from extended proximally by means of engagement of said flexible tongues 12 on the abutment surface 15a.

The time for the sealing cover 27 to move from its initial state to its final state allows the totality of the liquid to be expelled through the injection needle 6.

As shown on FIG. 6, the sleeve 16 continues to move distally, under the force exerted by said first helicoidal spring 24, until the sealing cover 27 comes in contact with the proximal end of said sleeve 16 and substantially all the pressurized fluid present in the chamber 26 has escaped via the vent outlet 19. During this movement, the outer radial rim 20 comes in contact with said flexible tongues 12 which are then caused to deflect radially and outwardly, as shown on FIG. 6. The radial wall 15 is therefore disengaged from said flexible tongues 12 and the second helicoidal spring 25 is free to move proximally. The force of said second helicoidal spring 25 being greater than the force of the first helicoidal spring 24, said second helicoidal spring 25 pushes said ring 14, which is coupled to said support 21 in the proximal direction, thanks to an outer rim 21c provided on said support 21 on which the proximal end 14a of said ring abuts.

The container 5 being fixed to said support 21, it is caused to move proximally and to retract within said distal cylinder 11 to reach its final position, within said housing (9, 11), as shown on FIG. 7.

Thanks to the temporizing means of the device of the invention, the retraction of the needle within the housing is an indication for a user that substantially all of the product contained within the container has been caused to pass through the outlet port of the injection needle 6.

In the final position, the needle 6 is contained within said housing (9, 11) and the device 1 is therefore ready to be disposed of, without any risk of accidental needlestick injury.

In an alternative embodiment of the invention not shown, the friction force of the sealing cover 27 against the inner walls of said sleeve 16 is such as allowing said sealing cover 27 to start moving from its initial state as soon as the injection begins.

In another embodiment of the invention not shown, the force of the first helicoidal spring 24 is reduced by adding a third spring for moving said sealing cover 27 from its initial state to its final state. Such an embodiment allows the reducing of the force with which the support 21 or the container 5 touches the inner ridge 13 or the injection site 4, especially the skin, and brings some comfort to the user.

On FIG. 8 is shown a variant of the device 1 of FIGS. 1 to 7, in which the sleeve forming the chamber is confounded with the push button. The references pertaining with the same elements as in FIGS. 1 to 7 have been retained.

As can be seen from FIG. 8, the deactivating means and the chamber are provided as a sleeve 30 which is closed at its proximal end. Said proximal end forms a pushing surface 30*a* for the user to exert a manual and distal pressure when he wishes to activate the device 1. The proximal end comprises a vent outlet 29*b*. A sealing cover 29*a* is provided on the head of a plunger rod 8.

The sleeve 30 is provided with at least an outer projection 31 and said housing 9 is provided with a stop 32. In the initial position of the container 5, said outer projection 31 is in abutment against said stop 32, said outer projection 31 and said stop 32 forming first retaining means of said container 5 in the initial position.

In steps not shown, after removal of the needle shield and the deshielder, the user applies the device 1 on the injection site and he pushes distally on pushing surface 30*a* causing said sleeve 30 to move distally. The manual pressure exerted on the sleeve 30 by the user overcomes said stop 32 and the first helicoidal spring 24 is then free to move distally. The first helicoidal spring 24 pushes on the outer radial rim 20 of said sleeve 30, thereby realising the insertion of the needle 6, the injection and the temporization as seen for the device 1 of FIGS. 1 to 7. The container 5 is caused to move from its insertion position to its final position by the second helicoidal spring 25 only when the sealing cover 29*a* has reached its final state by coming in contact with the proximal end of said sleeve 30.

On FIGS. 9 to 11 is shown another variant of the device 1 of the invention, in which the plunger rod is provided in two parts, a proximal part and a distal part, that separate when said piston comes into contact with the distal end of said container. The references pertaining with the same elements as in FIGS. 1 to 7 have been retained.

On FIG. 9 is shown a device 1 according to the invention comprising a plunger rod 40 provided in two parts, a proximal part 41 and a distal part 42. The proximal part 41 of the plunger rod 40 is provided at its proximal end with a head 49 and at its distal end with a radial projection 44. The distal part 42 of the plunger rod comprises a cylinder, the inner walls of which are coated with a rubbery material 43.

The housing 9 is provided on its inner wall with at least two radially flexible legs 46.

The device 1 further comprises a ring 48, said ring 48 being coupled to said container 5 when said container moves from its insertion position to its final position. Said ring 48 comprises an abutment surface 47.

On FIG. 9, the device 1 is in the injection position, said container 5 being in the insertion position. The first helicoidal spring 24 realizes the injection automatically by pushing distally the head 49 of the plunger rod 40. In this position, the force exerted by the first helicoidal spring 24 on the plunger rod 40 is not great enough to separate said plunger rod in two parts. The piston 7 is caused to move distally, thereby expelling the product 3 through the injection needle 6.

When said piston is proximate to the distal end of said container 5, as shown on FIG. 10, said distal part 42 of said plunger rod 40 is stopped but said proximal part 41 of said plunger rod 40 is allowed to continue its distal movement under the force exerted by said automatic injection means, that is to say the first helicoidal spring 24. The radial projection 44 comes then in contact with the rubbery material 43 and the distal movement of the proximal part 41 of the plunger rod 40 is slowed down, due to the interaction between the radial projection 44 and the rubbery material 43. Some time is then allowed for the totality of the product 3 to be expelled before retraction of the container 5 within the housing 9.

Actually, during the distal movement of the proximal part 41 of the plunger rod 40, the head 49 comes in contact with the flexible legs 46 of the housing 9 and cause them to be deflected radially. The abutment surface 47 is thereby disengaged from said flexible legs 46 and the second helicoidal spring 25 is free to return to its normal state and to extend in the proximal direction, as shown on FIG. 11.

The container 5 is only by then caused to move from its insertion position to its final position.

On FIGS. 12 to 17*c* are shown alternative temporizing means in the form of a plunger rod 40 provided in two parts, a proximal part 41 and a distal part 42. The references pertaining to the same elements as in FIGS. 9 to 11 have been retained.

Figure 12:
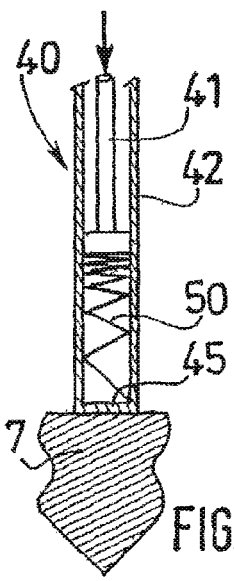
Figure 16:
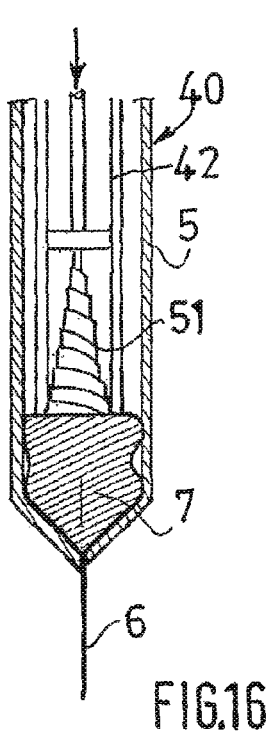

On FIGS. 12 and 16 are shown plunger rods 40 similar to that of FIGS. 9 to 11, in which the rubbery material has been replaced by a compressible material (50, 51): on FIG. 16, the compressible material is a spring 51. When the distal end of the proximal part 41 of the plunger rod 40 comes in contact with the compressible material (50, 51), the speed of the proximal part 41 of the plunger rod 40 is reduced and some time is therefore allowed for substantially all of the product to be expelled 3 before the head of the plunger rod cooperates with the second retaining means so as to cause the retraction of the container.

Figure 13:
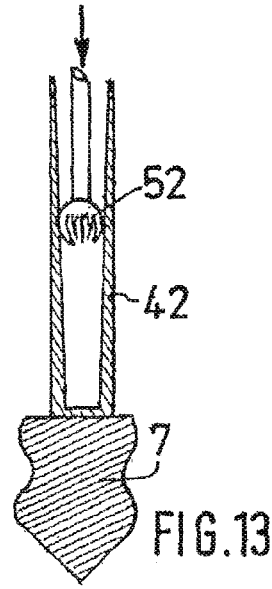

On FIG. 13 is shown a plunger rod 40 in two parts, wherein the diameter of the cylinder 42, which forms the distal part of the plunger rod, decreases towards the bottom of said cylinder. The distal end of the proximal part 41 of said plunger rod 40 is provided with flexible tongues 52 that rub against the inner walls of said cylinder, causing the proximal part 41 to be slowed down when it moves distally.

Figure 14:
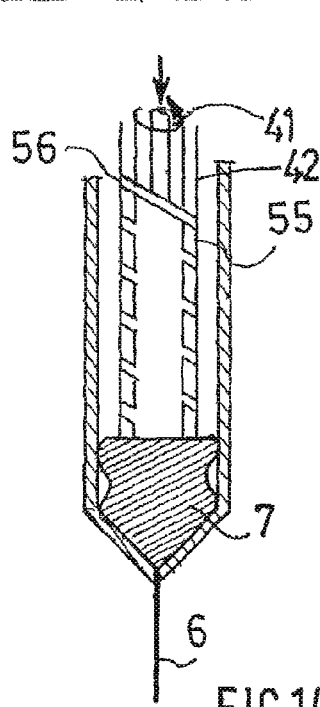

On FIG. 14, is shown a plunger rod 40 for which the inner walls of said cylinder 42 are provided with a thread 55 which cooperates with a screw 56 provided at the distal end of said proximal part 41 of said plunger rod, thereby reducing the speed of said proximal part 41 of said plunger rod, as said proximal part of said plunger rod moves distally.

Figure 15:
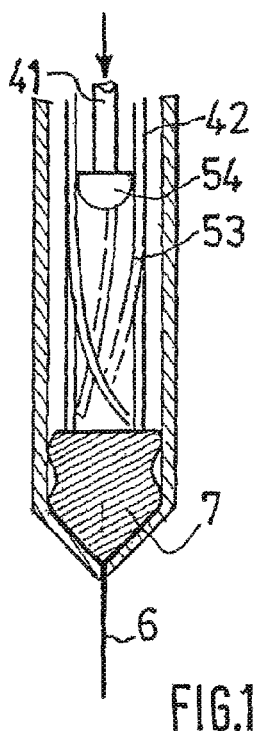

On FIG. 15 is shown a plunger rod 40 for which the inner walls of said cylinder 42 are provided with longitudinal flexible legs 53 that come in contact with a radial projection 54 provided at the distal end of said proximal part 41 of said plunger rod, thereby reducing the speed of said proximal part 41 of said plunger rod, as said proximal part of said plunger rod moves distally.

On FIGS. 17a to 17c is shown a plunger rod for which said cylinder walls are provided with a number of steps 57 and the distal end of said proximal part of said plunger rod is provided with a number of radial flaps 58, the number of radial flaps that interact with said steps increasing as said proximal part of said plunger rod moves distally.

On FIGS. 18 to 21 is shown an alternative embodiment of the device 1 of the invention. The reference numbers referring to the same elements as for FIGS. 1-7 have been retained.

The device 1 of FIGS. 18-21 comprises a chamber 59 partly defined by the inner part 61 of the container situated proximally to the piston 7. The rest of the chamber 59 is defined by the walls of the housing 68 receiving the container 5. A sealing cover 60 joins the proximal end 5b of said inner part 61 to the housing 68 through a friction force of absolute value F. At its proximal end, the chamber 59 comprises a vent outlet 63. The chamber 59 also comprises a recipient 65, preferably made of rigid walls.

In the initial position of the container, as shown on FIG. 18, this recipient 65 is sealingly closed and is filled with a pressurized fluid 64.

The device of FIGS. 18-21 further comprises a puncturing button 66 capable of creating an opening 67 in said recipient when a manual force is exerted on said puncturing button 66. The size of the opening 67 is much larger than the size of the vent outlet 63.

Moreover, the device 1 of FIGS. 18-21 comprises a sleeve 69 received within said housing 68 and receiving said container 5. The sleeve 69 comprises in its distal area an inner radial rim 70. A helical spring 62 is placed between said container 5 and said sleeve 69, the proximal end of said spring 62 bearing on the distal face of said proximal end of said container 5 and the distal end of said spring bearing on the proximal face of said inner radial rim 70 of said sleeve 69. The absolute value of the return force exerted by the spring 62 on said container 5 when said spring is at least in a partly compressed state is called Pe.

The functioning of the device 1 of FIGS. 18-21 will now be described.

The device 1 is provided to the user in its initial position shown on FIG. 18.

In this position, the needle 6 is protected by a needle shield 2 and a deshielder 2a.

The recipient 65 is filled with the pressurized fluid 64. When the user desires to proceed with the administration of the product 3, he removes the deshielder 2a and the needle shield 2, applies the device 1 on the injection site 4 and exerts a manual force on the puncturing button 66. The puncturing button 66 penetrates a wall of the recipient 65 and creates an opening 67 as shown on FIG. 19.

The pressurized fluid 64 is then allowed to escape the recipient 65 via the opening 67 and begins to fill the chamber 59. As shown on FIG. 19, as the pressurized fluid 64 spreads into the chamber 59, it pushes on the sealing cover 60 and therefore on the container 5 which is caused to move distally. By way of consequence, the needle 6 penetrates the injection site and the device 1 is in the insertion position. Once the distal movement of the container 5 is stopped, thanks to the proximal end 5b of said container 5 bearing on the distal end of the sleeve 69, the pressure exerted by the pressurized fluid 64 in the chamber 59 causes the piston 7 to move distally.

Figure 20:
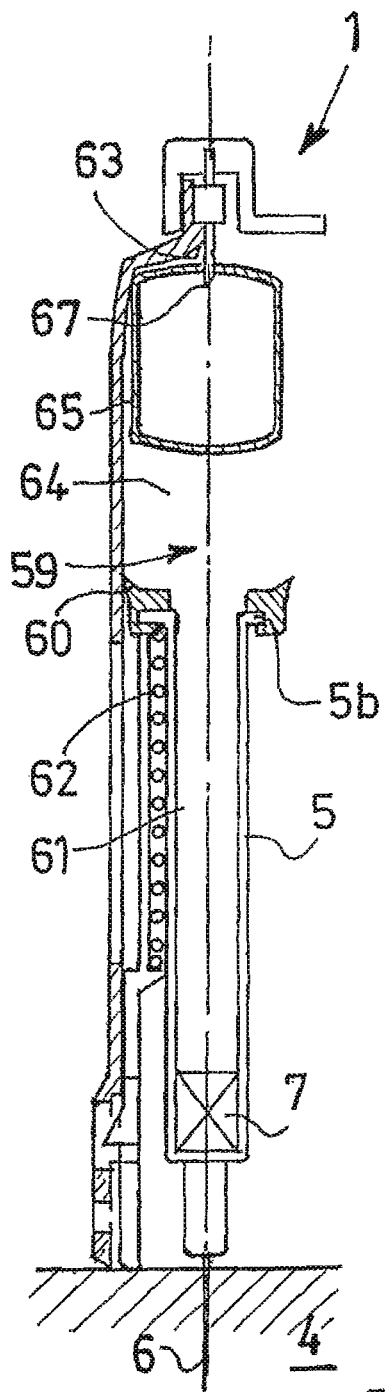
Figure 21:
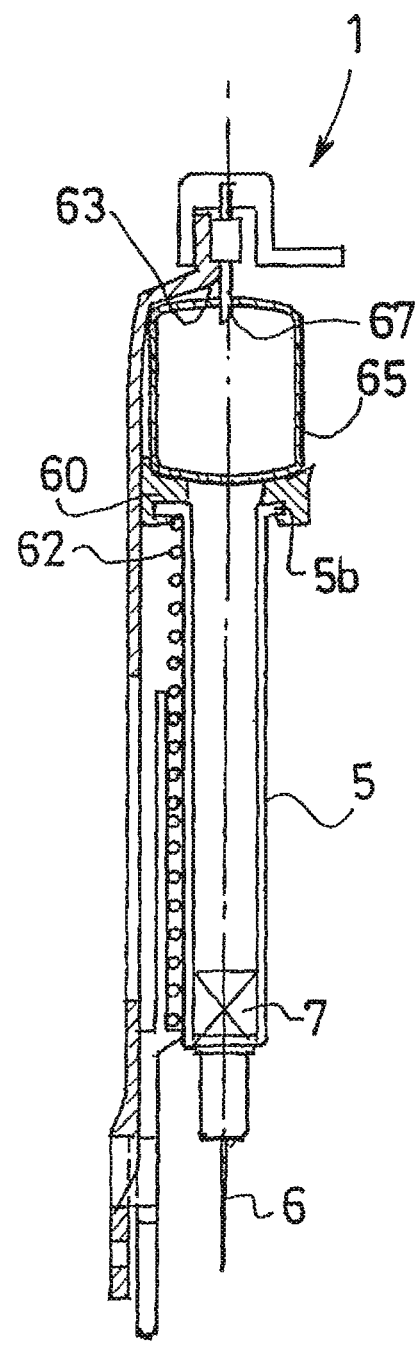

As the piston 7 moves distally, the product 3 is injected in the injection site 4 via the needle 6 until the piston 7 is proximate to the distal end of the container 5, as shown on FIG. 20.

During the insertion and the injection steps, some of the pressurized fluid 64 has been allowed to escape the chamber 59 via the vent outlet 63. Nevertheless, since the size of the vent outlet 63 is much smaller than the opening 67, only a negligible amount of pressurized fluid 64 has escaped from said chamber 59.

When the piston 7 is proximate to the distal end of the container 5, as shown on FIG. 20, the pressurized fluid 64 exerts a pressure on said container 5 of absolute value Pc.

During the injection step and until the piston 7 is proximate to the distal end of the container 5, Pc is greater than (Pe+F). As the pressurized fluid 64 escapes through the vent outlet 63, Pc decreases.

Moreover, during the insertion step, the spring 62 has been compressed and its return force Pe has increased.

Therefore, during the injection step, the retaining means are formed by Pc being greater than (Pe+F). When Pe becomes equal or greater than (Pc+F), the retaining means are released and the spring 62 is allowed to return to its expanded state. The time necessary for Pe to become equal or greater than (Pc+F) allows the injection to be totally completed.

The return of the spring 62 to its expanded state is subject to the flowing of the fluid 64 outside the chamber 59 via the vent outlet 63.

In consequence, due to the small size of the vent outlet 63, the return of the spring to its expanded state will occur slowly and the needle 6 will slowly retract within said housing 68.

On FIGS. 22 to 25 is shown an alternative of the embodiment of FIGS. 18-21.

The device 1 of FIGS. 22-25 comprises a chamber 79 partly defined by the inner part 71 of the container 5 situated proximally to the piston 7. The rest of the chamber 79 is defined by the walls of the housing 72 receiving the container 5 and by the head 73 of a piston rod 74. The distal end 77 of the piston rod 74 is not fixed to the piston 7.

A first sealing cover 75 joins the proximal end 5b of said inner part 71 to the housing 72. A second sealing cover 76 joins the head 73 of the piston rod 74 to the housing 72 and therefore seals the chamber 79. The two sealing covers (75, 76) are porous sealing cover. In consequence, they both form an outlet vent for any pressurized fluid comprised in the chamber 79. The two sealing covers (75, 76) present altogether a friction force against the wall of the housing 72 of absolute value F.

The device 1 of FIGS. 22-25 comprises a sleeve 78 received within said housing 72 and receiving said container 5. The sleeve 78 comprises in its distal area an inner radial rim 80. A helical spring 81 is placed between said container 5 and said sleeve 78, the proximal end of said spring 81 bearing on the distal face of said proximal end of said container 5 and the distal end of said spring bearing on the proximal face of said inner radial rim 80 of said sleeve 78. The absolute value of the return force exerted by the spring 81 on said container 5 when said spring is at least in a partly compressed state is called Pe.

The device 1 of FIGS. 22-25 further comprises a stop 82 provided on the inner wall of said housing 72. The device 1 also comprises a push button 83 having two distal legs 84.

The head 73 of the piston rod 74 is provided with two proximal flexible tongues 85. The proximal end of the housing 72 is provided with two abutment surfaces 86.

A helical spring 87 is provided within the push button 83 and the proximal part of the head 73 of the piston rod 74. The proximal end of the spring 87 bears on the distal face of the push button 83, and the distal end of the spring 87 bears on the proximal face of the proximal part of the head 73 of the piston rod 74. The absolute value of the return force exerted by the spring 87 on said piston rod 74 when said spring is at least in a partly compressed state is called Pi.

The functioning of the device 1 of FIGS. 22-25 will now be described.

Figure 22:
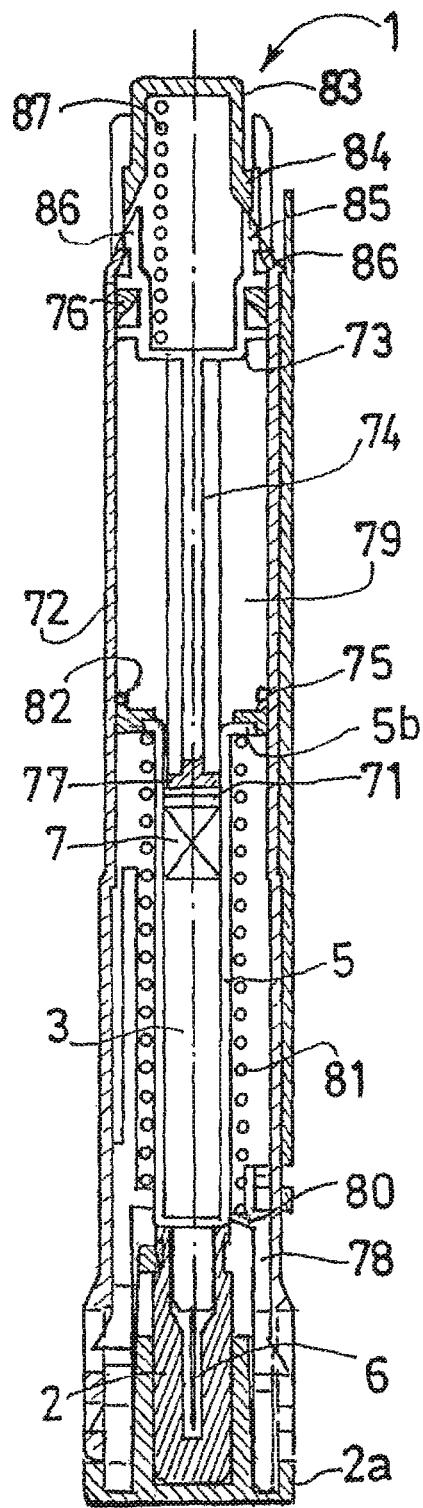
Figure 23:
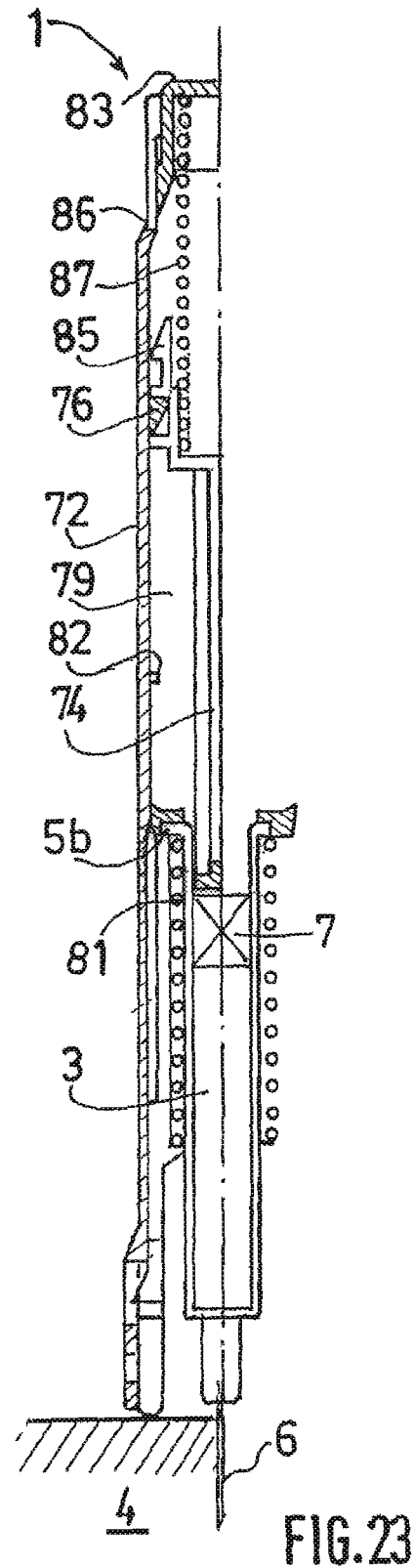

The device 1 is provided to the user in its initial position shown on FIG. 22.

In this position, the needle 6 is protected by a needle shield 2 and a deshielder 2a. The proximal tongues 85 of the head 73 of the piston rod 74 are engaged in the abutment surfaces 86 of the housing 72. The spring 87 is in a compressed state.

When the user desires to proceed with the administration of the product 3, he removes the deshielder 2a and the needle shield 2, applies the device 1 on the injection site 4 and exerts a manual force on the pushing button 83. The push button 83 therefore moves distally and its distal legs 84 come in contact with the flexible tongues 85 of the housing 72. Under the pressure of the distal legs 84, the flexible tongues 85 deflect radially and become disengaged from the abutment surfaces 86. The spring 87 is then free to return to its expanded state and it pushes the piston rod 74 in the distal direction. The friction F of the sealing covers (75, 76) being less than the friction force of the piston 7 against the inner wall of the container 5, said container 5 is drawn in the distal direction, thereby realising the insertion of the needle 6 in the injection site 4, as shown on FIG. 23.

Once the distal movement of the container 5 is stopped, thanks to the proximal end 5b of said container 5 bearing on the distal end of the sleeve 78, the force of the spring 87 overcomes the stiction force and the piston 7 is pushed distally by the distal end of the piston rod 74, therefore realising the injection of the product 3 into the injection site 4.

Figure 24:
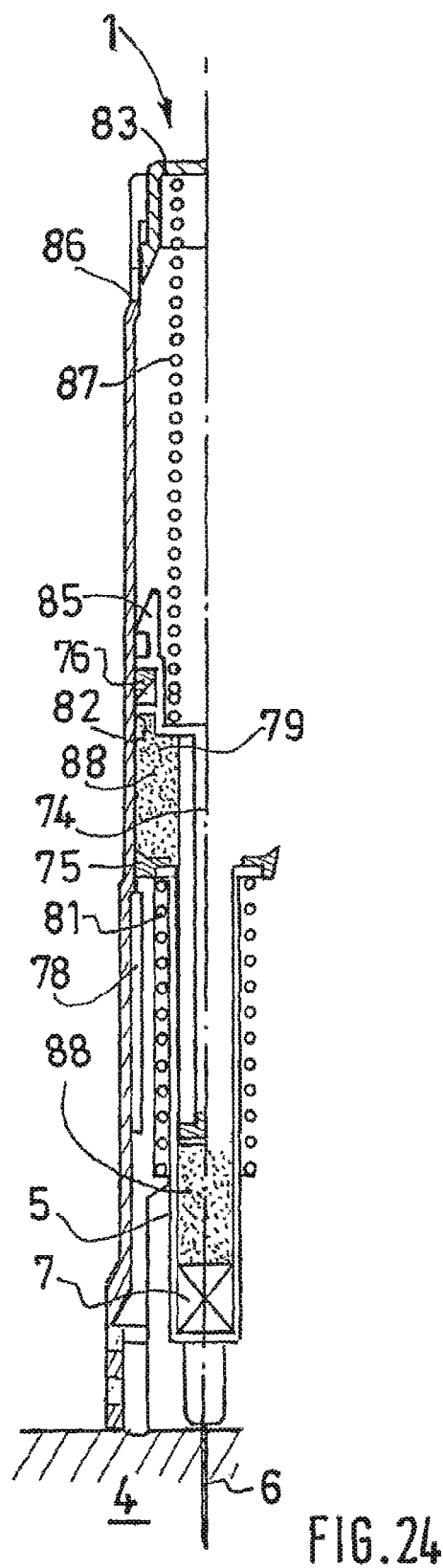
Figure 25:
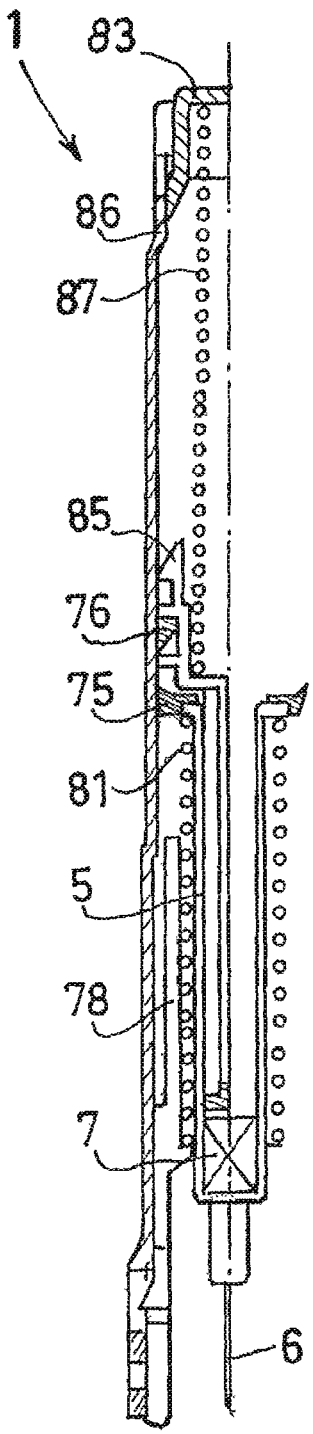

As the piston 7 and the piston rod 74 move distally, the volume defining the chamber 79 decreases, as shown on FIG. 24. In consequence, the fluid, for example the gas or the air, present within said chamber 79 becomes pressurized. Moreover, before the piston 7 comes proximate to the distal end of the container, as shown on FIG. 24, the distal movement of the piston rod 74 is stopped by the stop 82 provided on the inner wall of said housing 72. The pressurized fluid, referenced 88 on FIG. 24, fills therefore the space situated between the piston 7 and the distal end 77 of the piston rod 74, therefore maintaining the piston 7 against the distal end of the container 5 and allowing extra time for the injection to be totally completed. The pressure of the pressurized fluid 88 is called Pc.

During the insertion step, the spring 81 has been compressed and its return force Pe has increased.

During the injection step, and after the piston 7 comes proximate to the distal end of the container 5, the pressurized fluid escapes through the porous sealing covers (75, 76). Therefore, once the piston 7 has reached the very end of the distal end of the container 5 and substantially all of the product has been caused to pass through the outlet port of the injection needle 6, Pc decreases as a consequence of the fluid escaping the chamber 79 through the porous sealing covers (75, 76).

During the injection step, the retaining means are formed by (Pc+Pi) being greater than (Pe+F). When Pe becomes equal or greater than (Pc+F+Pi), the retaining means are released and the spring 81 is allowed to return to its expanded state. The time necessary for Pe to become equal or greater than (Pc+F+Pi) allows the injection to be totally completed.

By returning to its expanded state, the spring 81 draws the needle 6 back within the housing 72 and the device 1 is safe.

In reference to FIGS. 26 and 27 there is shown partial views of a deshielder 2a suitable as a tamper-evidence means for a device of the invention. The deshielder 2a is made of a cap 90 and a ring 91 connected to each other by breakable bridges 92.

In the pre-use condition, as shown on FIG. 26, the deshielder 2a is fixed on the housing 93 of a device according to the invention. The cap 90 and the ring 91 are made of a single piece, for example by moulding injection, and are connected to each other by means of the breakable bridges 92

The housing 93 is provided with stops 94 that prevent a user from breaking the bridges 92 by applying a proximal force on the cap 90.

When a user is ready to use the device of the invention, he removes the deshielder 2a by pulling distally on the cap 90 so as to remove it from the housing 93, thereby breaking the breakable bridges 92.

As can be seen on FIG. 27, the housing 93 is provided with grooves 95 that guide the translation of the cap 90 as it is removed. In this way, the deshielder and the needle shield (not shown) which is within the cap 90, are removed with limited or no rotation of the needle (not shown). Coring caused by the tip of the needle rotating in the rubber forming the needle shield is therefore prevented.

On FIG. 27, the tamper-evidence means formed by the deshielder 2a is in its post-use condition. Any user, provided with the device with the deshielder 2a in this condition can immediately notice, thanks to the broken bridges 92, that the device has been tampered. The post-use condition of the deshielder proves an indication that the tamper-evidence means has been removed from the device.

Moreover, because of the broken bridges 92, it is impossible for anybody to replace the cap in its pre-use condition.

On FIG. 28 is shown a tray 400 for carrying upper housing assemblies 100 in a predetermined direction. The carrying means 400 of FIG. 28 can especially carry a plurality of upper housings 100, all disposed in the same direction. Such a tray comprises a plurality of holes 402 intended to receive the upper housing assemblies 100. Such a tray 400 is useful for transporting and/or handling upper housings of a device of the invention during all the various steps of manufacturing, filling, packaging, etc. . . . .

On FIG. 29 is shown a tray 401 similar to the tray 400 of FIG. 28, the tray 401 carrying, in the example shown a plurality of lower housing assemblies 200 of a device of the invention, in a predetermined orientation.

On FIGS. 30-33 is shown a variant of the device of FIGS. 22-25. The references designing the same elements as in FIGS. 22-25 have been retained.

The device 1 of FIGS. 30-33 comprises a chamber 96 partly defined by the inner part 71 of the container 5 situated proximally to the piston 7. The rest of the chamber 96 is defined by the walls of the housing 72 receiving the container 5 and by the head 73 of a piston rod 74. The distal end 77 of the piston rod 74 is not fixed to the piston 7.

A first sealing cover 97 joins the proximal end 5b of said inner part 71 to the housing 72. A second sealing cover 98 joins the head 73 of the piston rod 74 to the housing 72 and therefore seals the chamber 96. The two sealing covers (97, 98) are porous sealing cover. In consequence, they both form an outlet vent for any pressurized fluid comprised in the chamber 96. The two sealing covers (97, 98) present altogether a friction force against the wall of the housing 72 of absolute value F.

The device 1 of FIG. 30-33 comprises a sleeve 102 received within said housing 72 and receiving said container 5. The sleeve 102 comprises in its distal area an inner radial rim 103 and at its proximal end a flexible tongue 104 provided with an abutment surface 105. A helical spring 106 is placed between said container 5 and said sleeve 102, the proximal end of said spring 106 bearing on the distal face of said abutment surface 105 by the intermediary of a ring 107 and the distal end of said spring 106 bearing on the proximal face of said inner radial rim 103 of said sleeve 102.

The device 1 of FIGS. 30-33 further comprises a push button 83 having two distal legs 84.

The head 73 of the piston rod 74 is provided with two proximal flexible tongues 85. The proximal end of the housing 72 is provided with two abutment surfaces 86.

A helical spring 87 is provided within the push button 83 and the proximal part of the head 73 of the piston rod 74. The proximal end of the spring 87 bears on the distal face of the push button 83, and the distal end of the spring 87 bears on the proximal face of the proximal part of the head 73 of the piston rod 74.

The functioning of the device 1 of FIGS. 30-33 will now be described.

Figure 30:
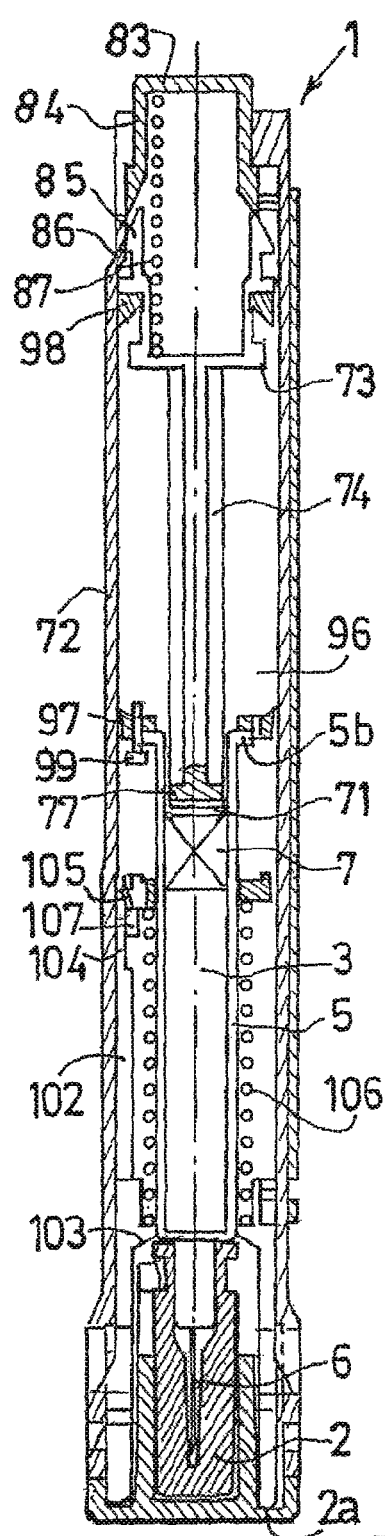
Figure 31:
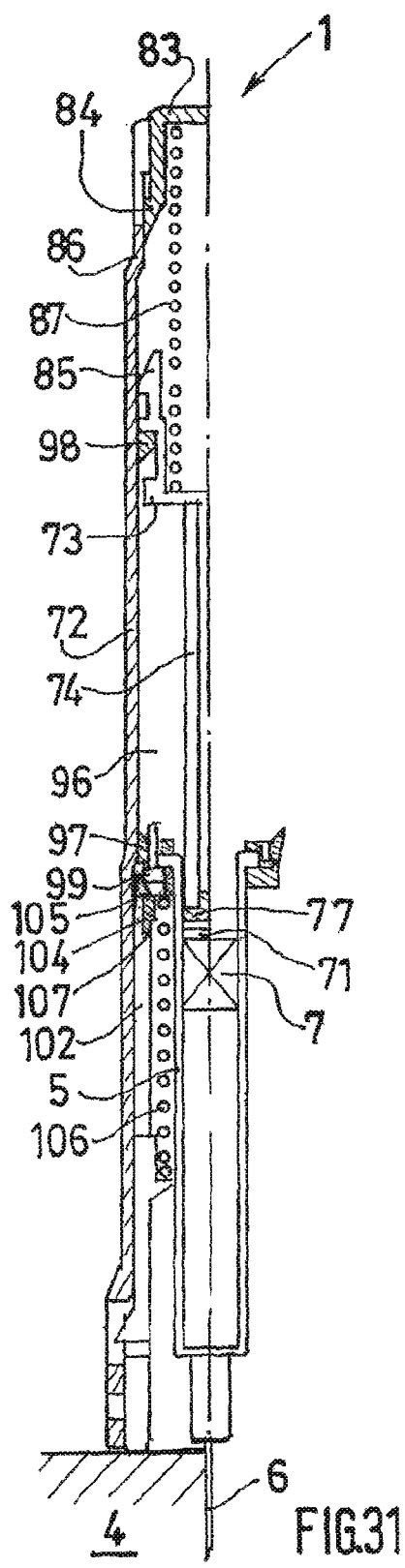
Figure 32:
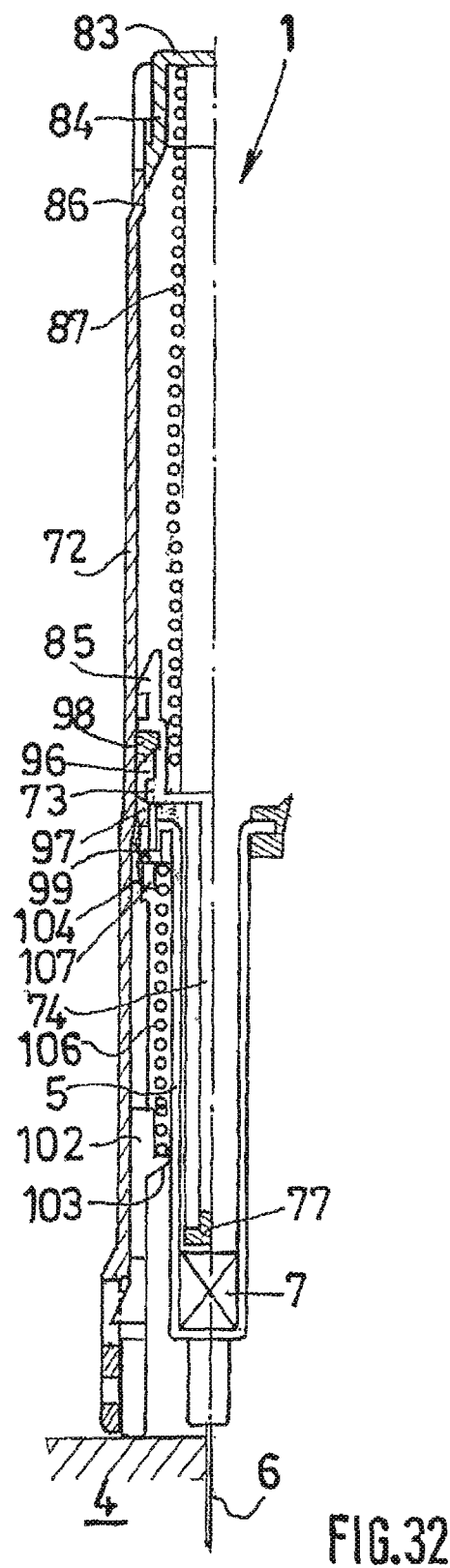

The device 1 is provided to the user in its initial position shown on FIG. 30.

in this position, the needle 6 is protected by a needle shield 2 and a deshielder 2a. The proximal tongues 85 of the head 73 of the piston rod 74 are engaged in the abutment surfaces 86 of the housing 72. The spring 87 is in a compressed state.

When the user desires to proceed with the administration of the product 3, he removes the deshielder 2a and the needle shield 2, applies the device 1 on the injection site 4 and exerts a manual force on the pushing button 83. The push button 83 therefore moves distally and its distal legs 84 come in contact with the flexible tongues 85 of the housing 72. Under the pressure of the distal legs 84, the flexible tongues 85 deflect radially and become disengaged from the abutment surfaces 86. The spring 87 is then free to return to its expanded state and it pushes the piston rod 74 in the distal direction. The friction F of the sealing covers (97, 98) being less than the friction force of the piston 7 against the inner wall of the container 5, said container 5 is drawn in the distal direction, thereby realising the insertion of the needle 6 in the injection site 4, as shown on FIG. 31.

Once the distal movement of the container 5 is stopped, for instance by the distal end of the container 5 coming in contact with the injection site 4, the force of the spring 87 overcomes the stiction force and the piston 7 is pushed distally by the distal end of the piston rod 74, therefore realising the injection of the product 3 into the injection site 4.

As the piston 7 and the piston rod 74 move distally, the volume defining the chamber 96 decreases. In consequence, the fluid, for example the gas or the air, present within said chamber 96 becomes pressurized. This fluid fills the space situated between the piston and the distal end 77 of the piston rod 74. Because of this space, when the piston 7 comes proximate to the distal end of the contained 5, the head 73 of the piston rod 74 is not in contact with the sealing cover 97. The porosity of the sealing covers (97, 98) allows said sealing covers to act as a vent outlet and some of the pressurized fluid present in the chamber 96 is allowed to escape said chamber 96 slowly, giving sufficient time for substantially all of the product 3 to be ejected. As substantially all of the product is ejected, the piston rod 74 is allowed to move slowly distally, and the head 73 of the piston rod 74 comes in contact with the valve 99 of the scaling cover 97. The valve 99 is pushed distally and comes in contact with the flexible tongue 104 which deflects radially, freeing the ring 107 and the spring 106. The freed spring 106 begins to moves proximally but it is slowed down by the force of the pressurized fluid present in the chamber 96. With the proximal movement of the spring 106, the ring 107 comes in contact with the valve 99 and opens it. The pressurized fluid still present in the chamber 96 is then allowed to escape via the open valve 99 and the spring 106 returns rapidly to its expanded state.

Figure 33:
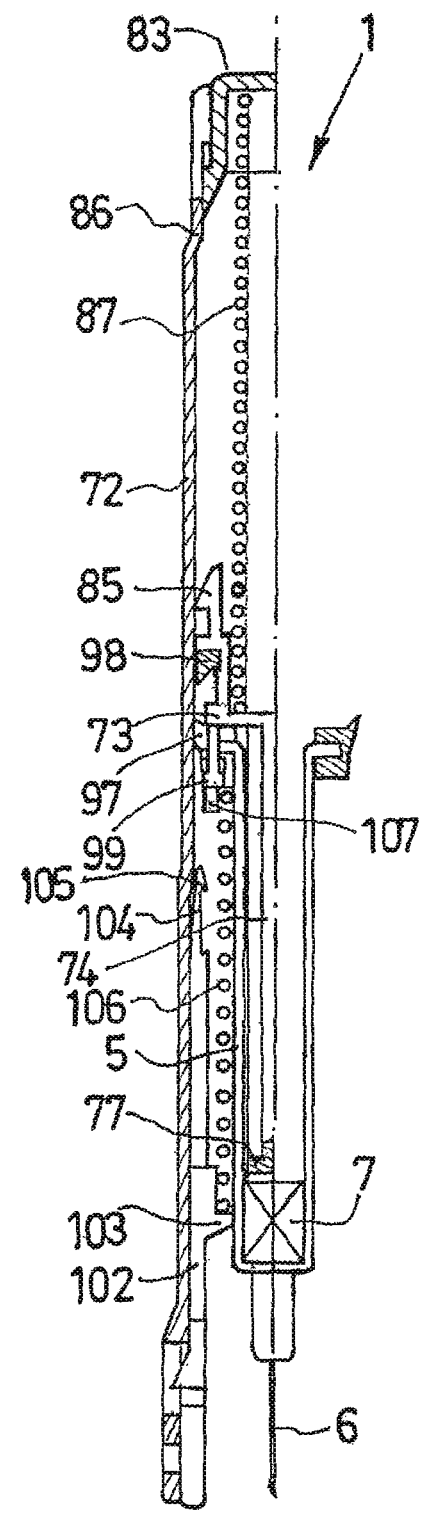

By returning to its expanded state, the spring 106 draws the needle 6 back into the housing 72 and the device is safe as shown on FIG. 33.

The device of the invention is very easy to use and very safe. It allows automatic injection of a product to be performed by a patient without any risk of needlestick injury, before, during and after use. In particular, it allows the retraction of the needle within the device only once substantially all of the product has been injected. Injections of improper doses of product are therefore prevented.

What is claimed is:

1. A device for automatic injection of a product into an injection site, the injection device comprising:
   a container having an open proximal end and a substantially closed distal end and being intended to receive a product, an injection needle being provided at said distal end;
   a housing intended to receive, at least partially, said container, said container being movable relative to said housing between an initial position, in which said needle is contained within said housing, an insertion position, distally spaced relative to said initial position and in which said needle is exposed over a predetermined length, and a final position in which said needle is contained within said housing; and,
   a collapsible chamber defined within said housing and outside of said container, said chamber being collapsible with said container in said insertion position, said chamber being at least partially defined by a proximal wall and a seal element, wherein, with said container in said initial position, said proximal wall is spaced proximally from said seal element and said chamber is filled with a fluid, wherein, with said container in said insertion position, said fluid is at least partially expelled from said chamber and said proximal wall is caused to engage said seal element, and, wherein, with said proximal wall engaging said seal element, said container being caused to move from said insertion position to said final position.

2. A device as in claim 1, wherein product contained within said container is expelled through said needle with said container in said insertion position, and, wherein, said chamber begins to collapse during expulsion of the product from said container.

3. A device as in claim 2, wherein, said proximal wall being caused to engage said seal element after complete expulsion of the product from said container.

4. A device as in claim 2, further comprising a piston slidably disposed within said container configured to expel the product and a sleeve configured to urge said piston.

5. A device as in claim 4, wherein sufficient distal movement of said sleeve causes said chamber to collapse.

6. A device as in claim 4, wherein, with said piston being located at a distal most position in said container with no ability for further distal movement relative to said container, said sleeve being configured to move distally to cause said proximal wall to engage said seal element.

7. A device as in claim 6, wherein said sleeve defines said proximal wall.

8. A device as in claim 4, wherein said sleeve defines said proximal wall.

9. A device as in claim 1, wherein said fluid is selected from the group consisting of a pressurized gas and a viscous liquid.

\* \* \* \* \*